(12) United States Patent
Bhirud et al.

(10) Patent No.: US 9,550,735 B2
(45) Date of Patent: Jan. 24, 2017

(54) PROCESS FOR THE PREPARATION OF IVACAFTOR AND SOLVATES THEREOF

(71) Applicant: GLENMARK PHARMACEUTICALS LIMITED; GLENMARK GENERICS LIMITED, (East) Mumbai (IN)

(72) Inventors: Shekhar Bhaskar Bhirud, Mumbai (IN); Samir Naik, Thane (IN); Sachin Srivastava, Navi Mumbai (IN); Ramesh Santosh Badgujar, Thane (IN); Sachin Lad, Thane (IN); Sukumar Sinha, Navi Mumbai (IN); Mohammad Amjed Khan, Navi Mumbai (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 14/764,311

(22) PCT Filed: Jan. 30, 2014

(86) PCT No.: PCT/IN2014/000071
§ 371 (c)(1),
(2) Date: Jul. 29, 2015

(87) PCT Pub. No.: WO2014/118805
PCT Pub. Date: Aug. 7, 2014

(65) Prior Publication Data
US 2015/0376134 A1    Dec. 31, 2015

(30) Foreign Application Priority Data

Jan. 31, 2013  (IN) .......................... 288/MUM/2013
Mar. 25, 2013  (IN) ........................ 1115/MUM/2013
Jul. 18, 2013  (IN) ........................ 2407/MUM/2013

(51) Int. Cl.
*C07D 215/56*      (2006.01)
*A61K 31/47*       (2006.01)

(52) U.S. Cl.
CPC ............ *C07D 215/56* (2013.01); *A61K 31/47* (2013.01)

(58) Field of Classification Search
CPC .............................. C07D 215/56; A61K 21/47
See application file for complete search history.

(56) References Cited

U.S. PATENT DOCUMENTS 7,495,103 B2    2/2009    Hadida-Ruah et al.

FOREIGN PATENT DOCUMENTS

| EP | 2502913 A2 | 9/2012 |
|---|---|---|
| WO | 2007079139 A2 | 7/2007 |
| WO | 2009038683 A2 | 3/2009 |

*Primary Examiner* — D M Seaman
(74) *Attorney, Agent, or Firm* — Ryan, Mason & Lewis, LLP

(57) ABSTRACT

The present invention provides process for the preparation of ivacaftor and solvates thereof.

12 Claims, 18 Drawing Sheets

PROCESS FOR THE PREPARATION OF IVACAFTOR AND SOLVATES THEREOF

PRIORITY

Figure 1:
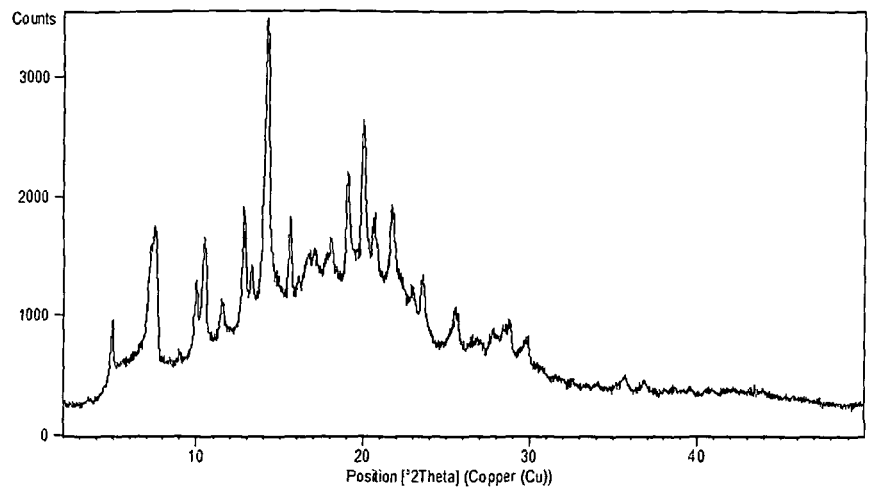

This application claims priority under 35 U.S.C. §371 to International Application No. PCT/IN2014/000071, filed Jan. 30, 2014 which claims the benefit under 35 U.S.C. §119 to Indian Provisional Applications Numbers 288/MUM/2013, filed Jan. 31, 2013, 115/MUM/2013, filed Mar. 25, 2013 and 2407/MUM/2013, filed Jul. 18, 2013 entitled "PROCESS FOR PREPARATION OF IVACAFTOR", the contents of which are incorporated herein by reference.

TECHNICAL FIELD

This invention relates to various forms of ivacaftor.

BACKGROUND

Ivacaftor which is chemically known as N-(2,4-di-tert-butyl-5-hydroxyphenyl)-1,4-dihydro-4-oxoquiniline-3-carboxamide is represented structurally by a compound of formula I.

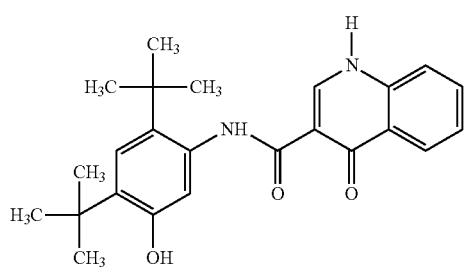

Ivacaftor is classified as a cystic fibrosis transmembrane conductance regulator potentiator. Ivacaftor is commercially available as Kalydeco® in the form of pharmaceutical preparations. Kalydeco® is indicated for the treatment of cystic fibrosis in patients age 6 years and older who have a G55ID mutation in the CFTR gene.

U.S. Pat. No. 7,495,103 discloses ivacaftor, a process for its preparation and its intermediates, wherein the process utilizes column chromatography and high performance liquid chromatography (HPLC) purification processes.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. Additionally, polymorphic forms of the same drug substance or active pharmaceutical ingredient, can be administered by itself or formulated as a drug product (also known as the final or finished dosage form), and are well known in the pharmaceutical art to affect, for example, the solubility, stability, flowability, tractability and compressibility of drug substances and the safety and efficacy of drug products. Therefore, there is a continuing need for new crystalline forms and new processes of preparing crystalline forms.

The present invention relates to various forms of ivacaftor.

SUMMARY OF THE INVENTION

In one embodiment, the present invention provides crystalline ivacaftor.n-butanol solvate.

In one embodiment, the present invention provides crystalline ivacaftor.n-butanol solvate characterized by X-ray Diffraction (XRD) spectrum having peak reflections at about 3.4 and 14.2±0.2 degrees 2 theta.

In one embodiment, the present invention provides crystalline ivacaftor.methanol solvate characterized by X-ray Diffraction (XRD) spectrum having peak reflections at about 7.2, 13.8, 14.0, 19.8 and 20.9±0.2 degrees 2 theta.

In one embodiment, the present invention provides a process for the preparation of ivacaftor, a compound of formula I, in amorphous form, the process comprising:

(a) dissolving a solvate of ivacaftor in a solvent to form a solution; and (b) removing the solvent from the solution obtained in (a).

In one embodiment, the present invention provides a process for the preparation of crystalline ivacaftor.n-butanol solvate comprising:

a) treating ivacaftor or a solvate thereof with a n-butanol, b) optionally, heating the above mixture of step 'a';

c) cooling the above mixture of step 'b'; and d) isolating crystalline ivacaftor.n-butanol solvate.

In one embodiment, the present invention provides a process for the preparation of crystalline ivacaftor.methanol solvate comprising:

a) treating ivacaftor with methanol to obtain a mixture;

b) optionally, heating the above mixture of step 'a';

c) cooling the above mixture of step 'b'; and d) isolating ivacaftor methanol solvate.

In one embodiment, the present invention provides amorphous ivacaftor free of gentoxic impurities, compounds of formula XI, II, VIII, XIV, VII, XV and XVI.

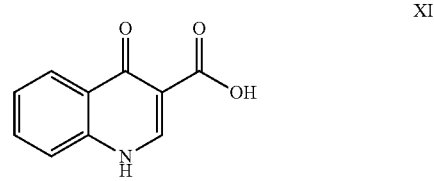 [SMILES: O=C(O)c1c[nH]c2ccccc2c1=O]

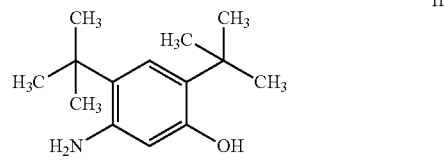

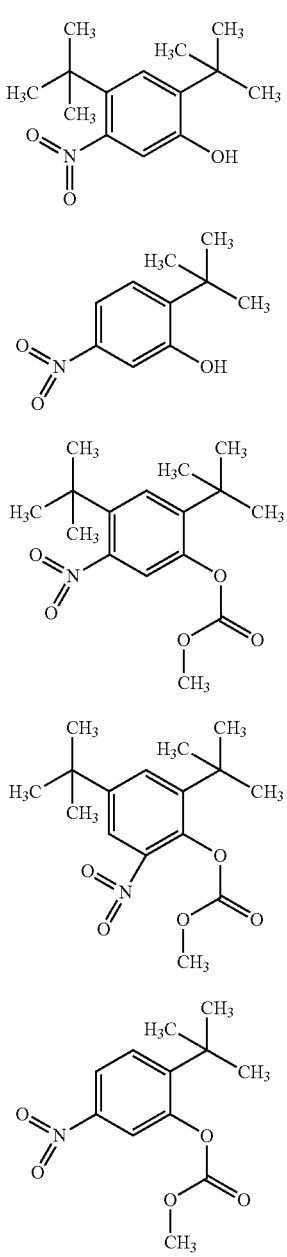

VIII

XIV

VII

XV

XVI

BRIEF DESCRIPTION OF THE
ACCOMPANYING FIGURES

FIG. 1: XRD pattern of ivacaftor Form G', according to example 1.

Figure 2:
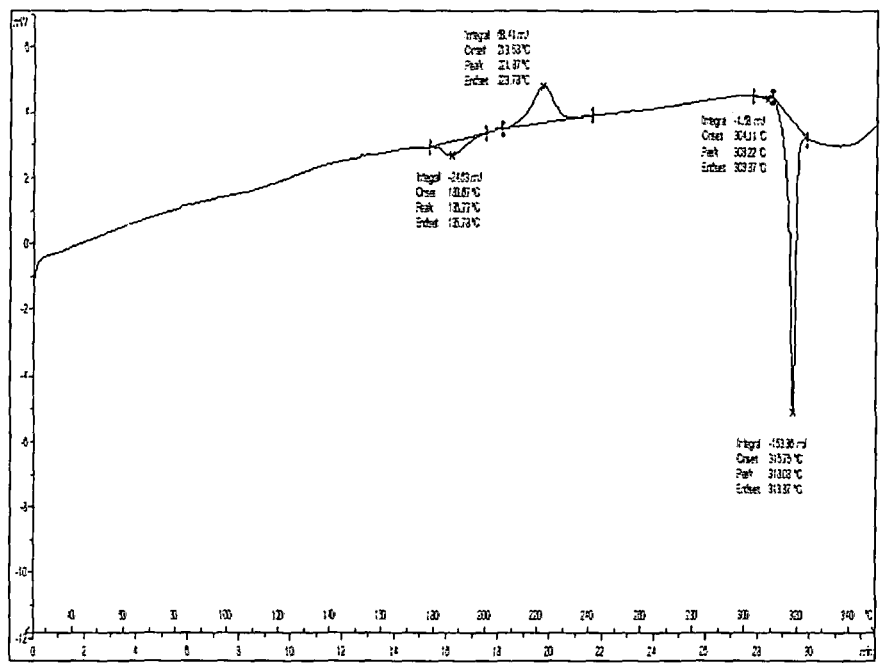

FIG. 2: DSC diffractogram of ivacaftor Form G', according to example 1.

Figure 3:
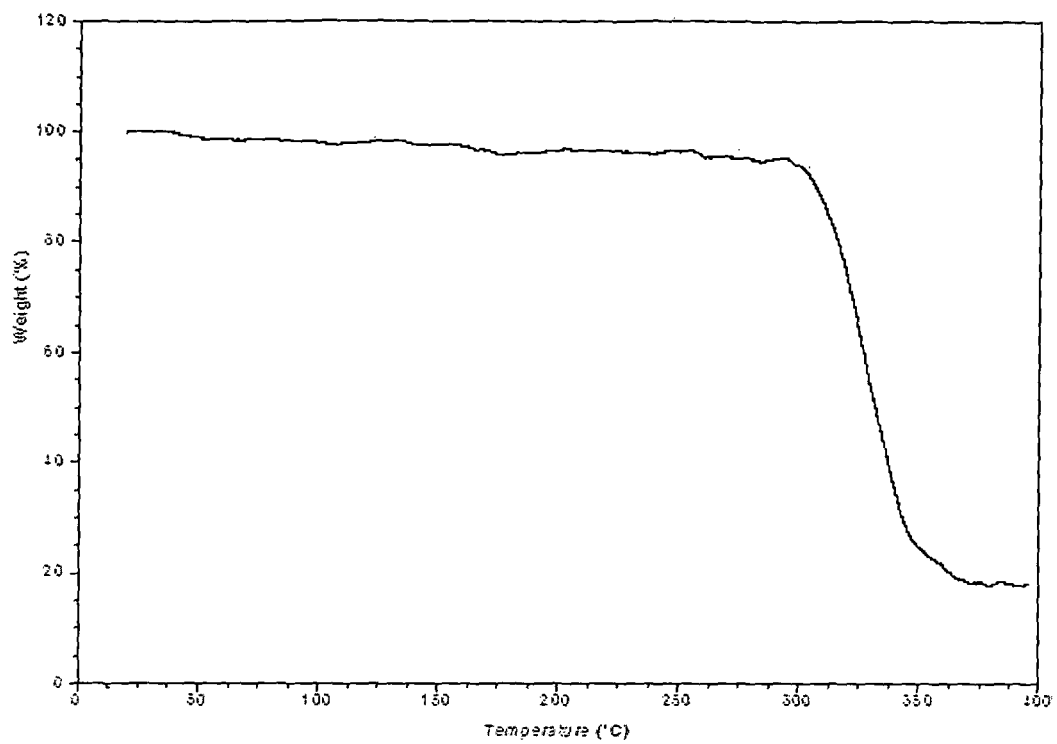

FIG. 3: TGA thermogram of ivacaftor Form G', according to example 1.

Figure 4:
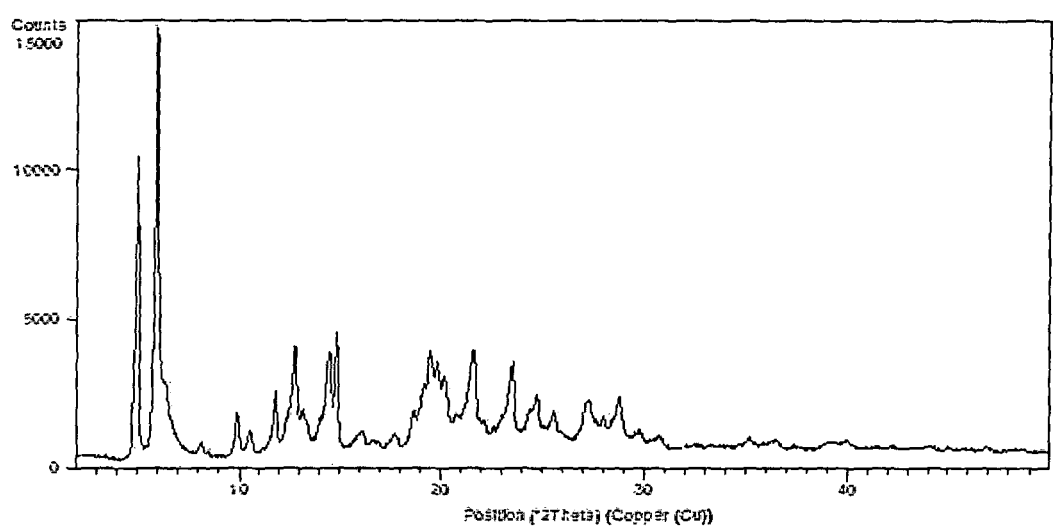

FIG. 4: XRD pattern of ivacaftor.n-butanol solvate, according to example 2.

Figure 5:
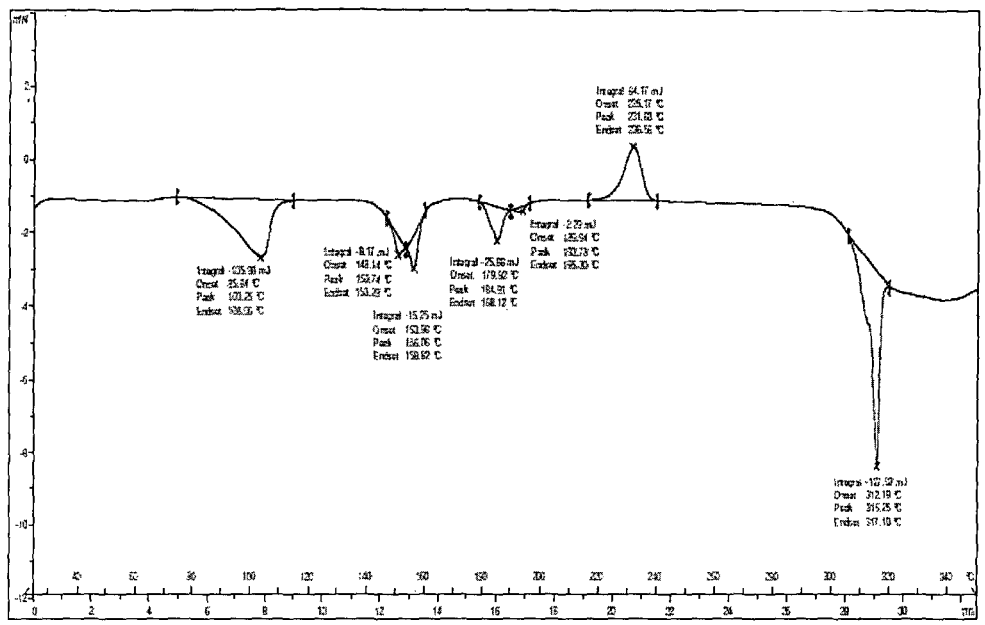

FIG. 5: DSC diffractogram of ivacaftor.n-butanol solvate, according to example 2.

Figure 6:
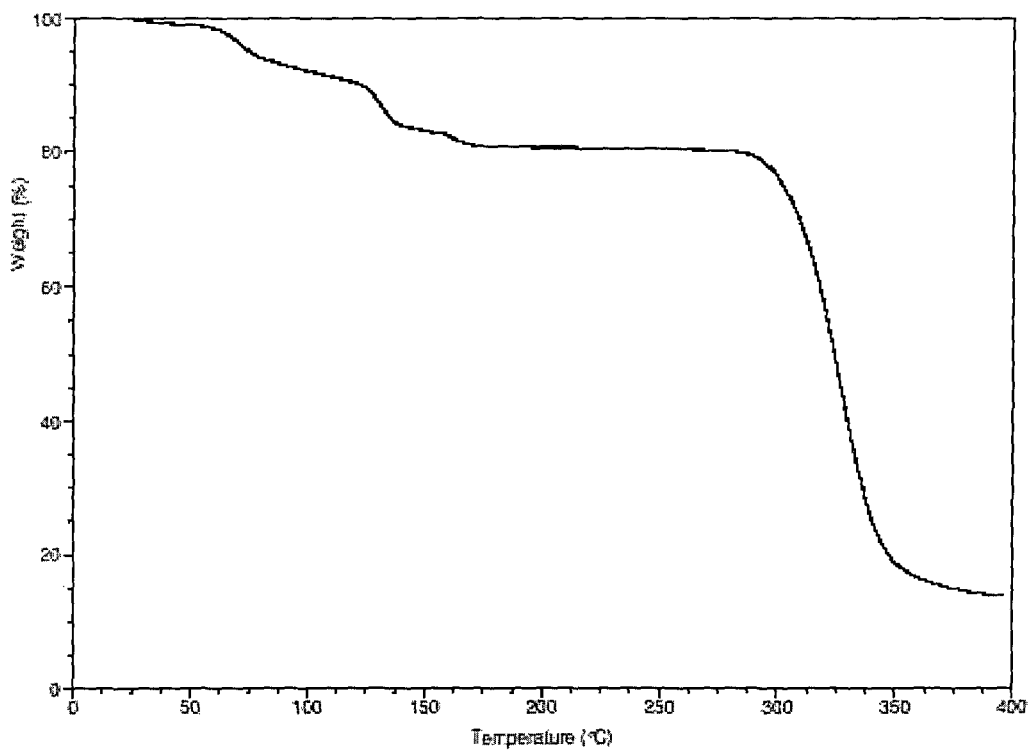

FIG. 6: TGA thermogram of ivacaftor.n-butanol solvate, according to example 2.

Figure 7:
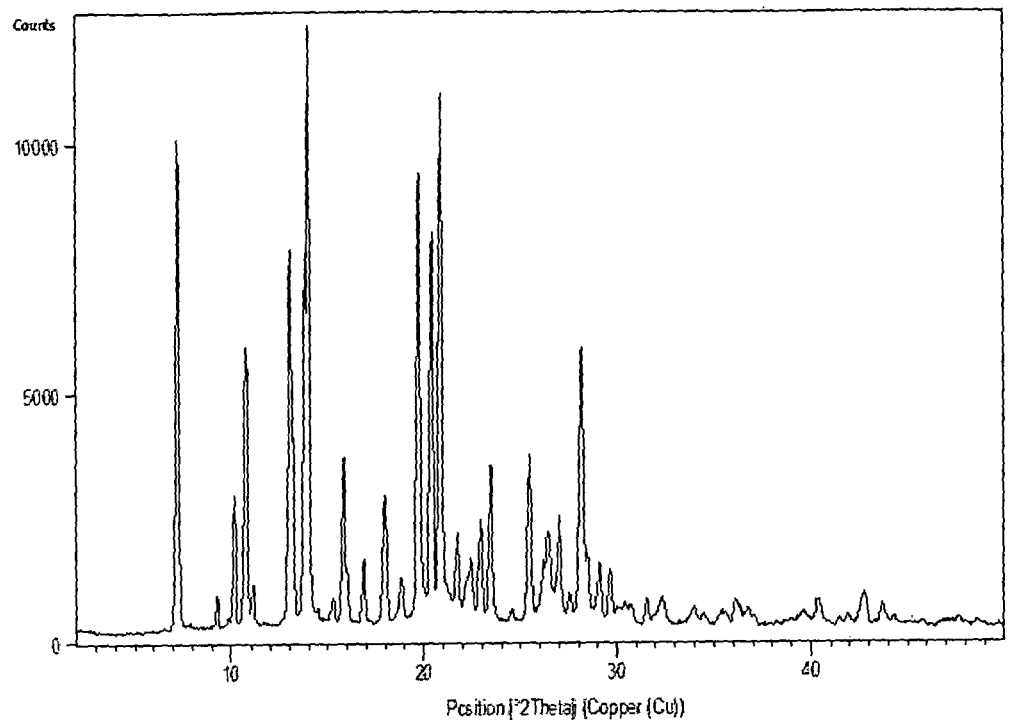

FIG. 7: XRD pattern of ivacaftor.methanol solvate according to example 3.

Figure 8:
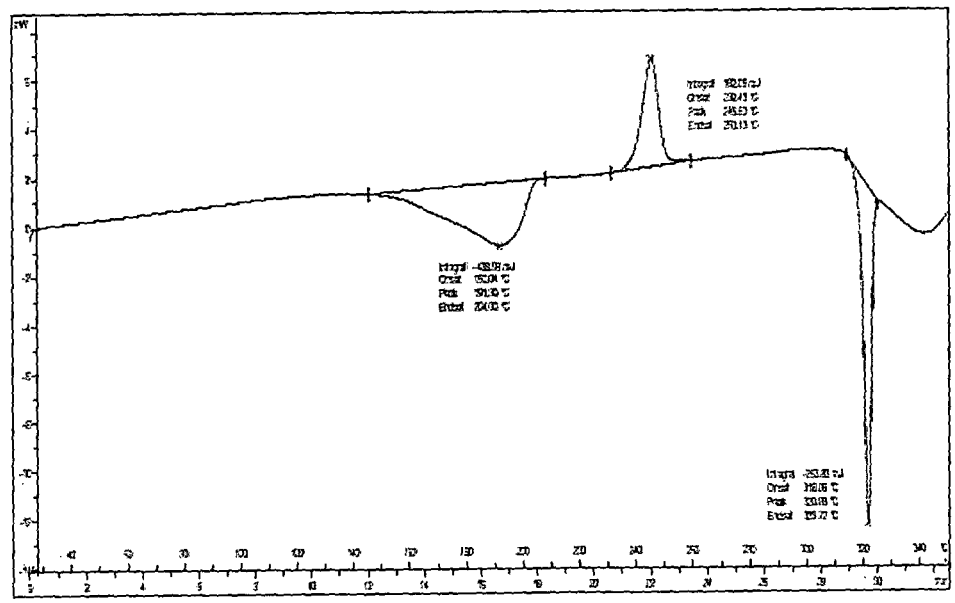

FIG. 8: DSC diffractogram of ivacaftor.methanol solvate, according to example 3.

Figure 9:
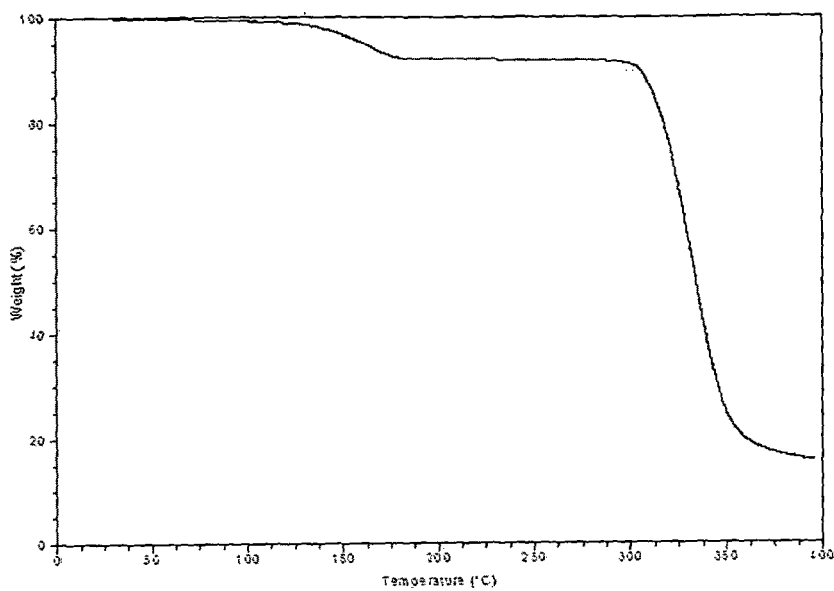

FIG. 9: TGA thermogram of ivacaftor.methanol solvate, according to example 3.

Figure 10:
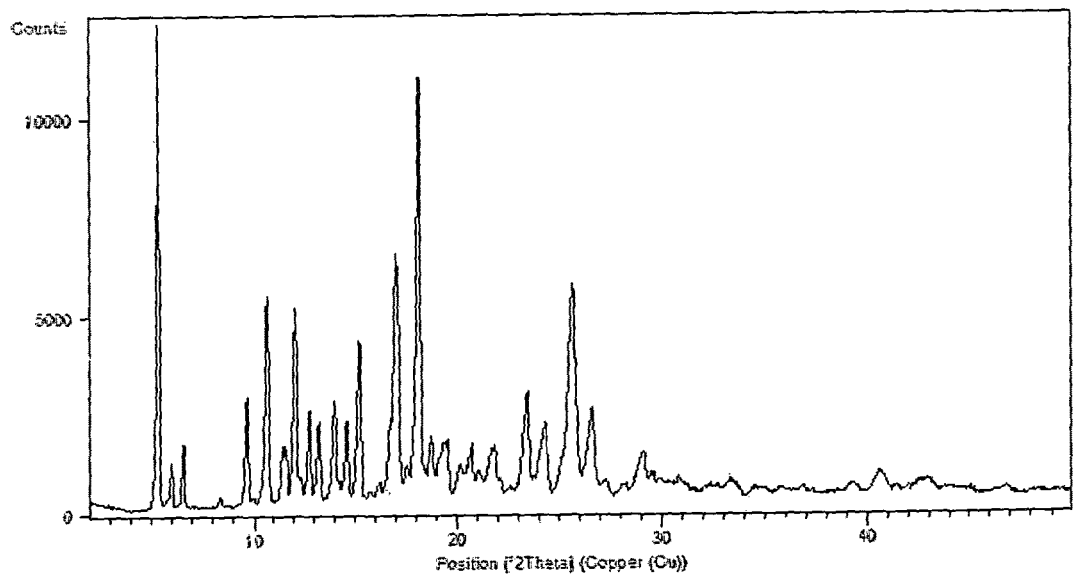

FIG. 10: XRD pattern of ivacaftor Form G according to example 4.

Figure 11:
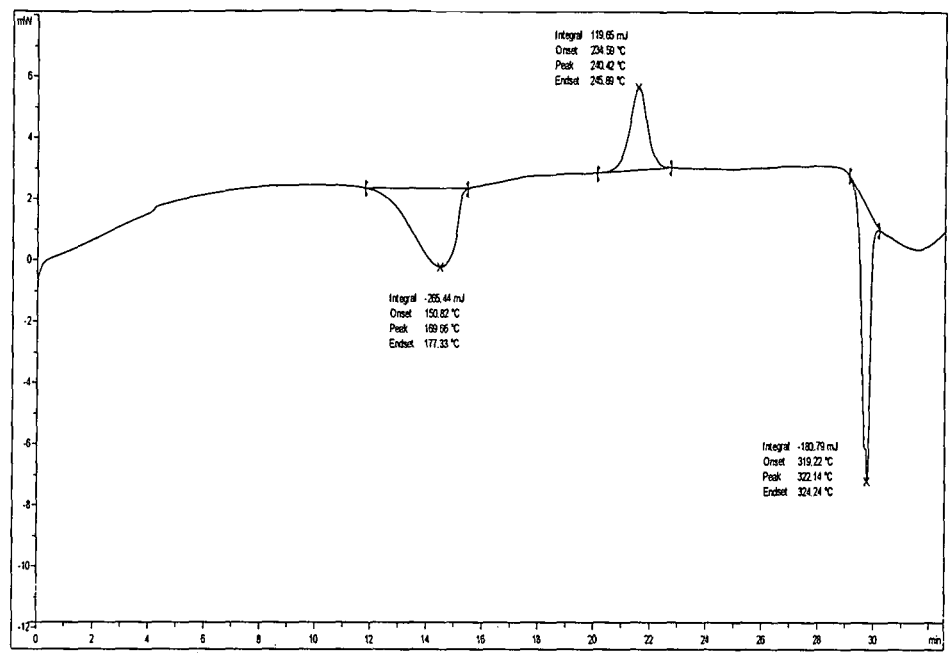

FIG. 11: DSC diffractogram of ivacaftor Form G, according to example 4.

Figure 12:
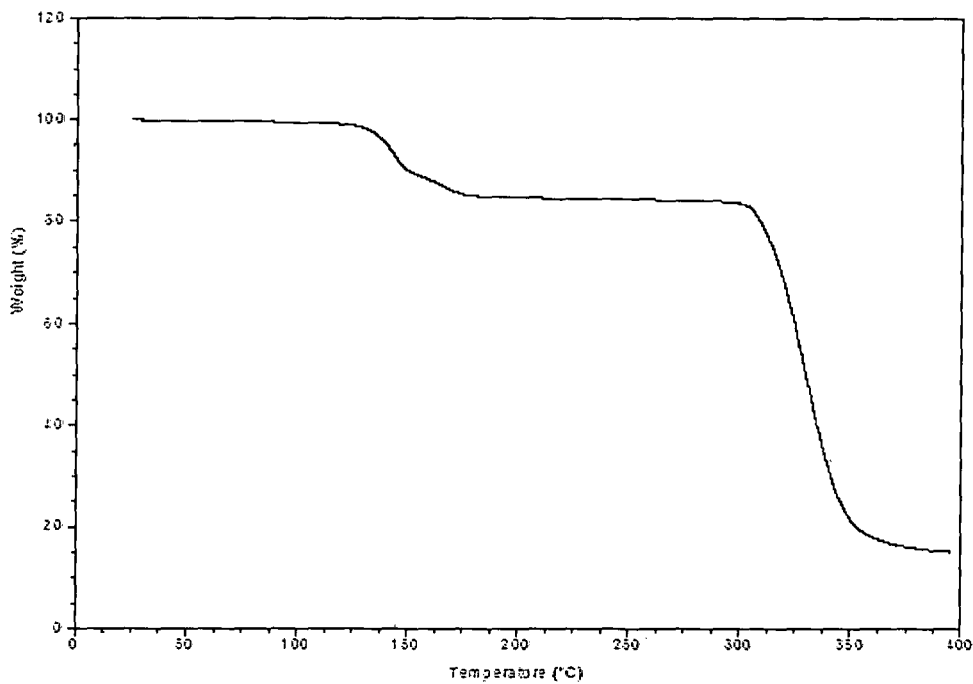

FIG. 12: TGA thermogram of ivacaftor Form G, according to example 4.

Figure 13:
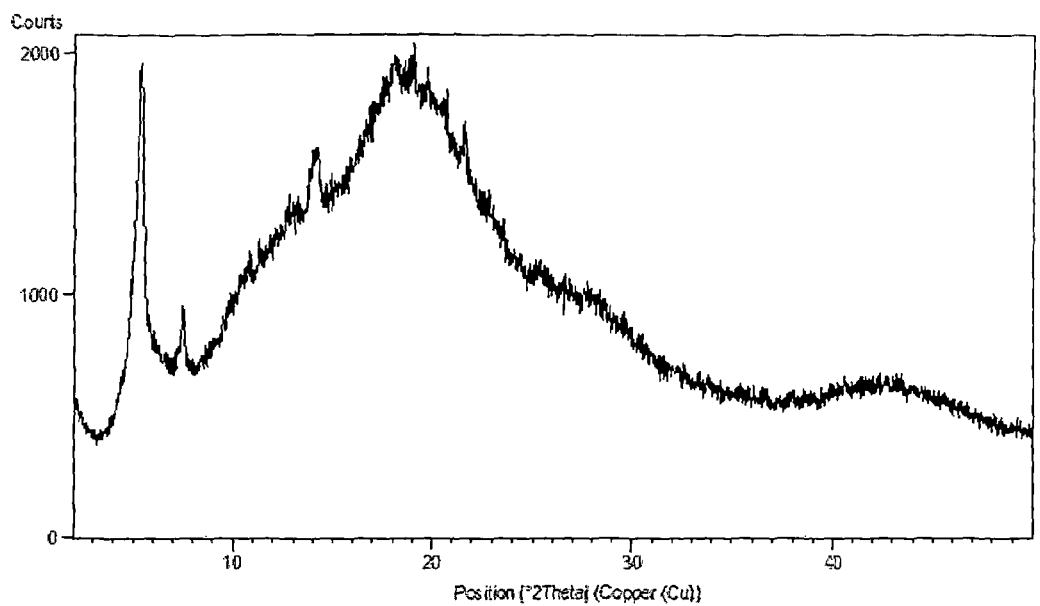

FIG. 13: XRD pattern of ivacaftor amorphous form I according to example 5.

Figure 14:
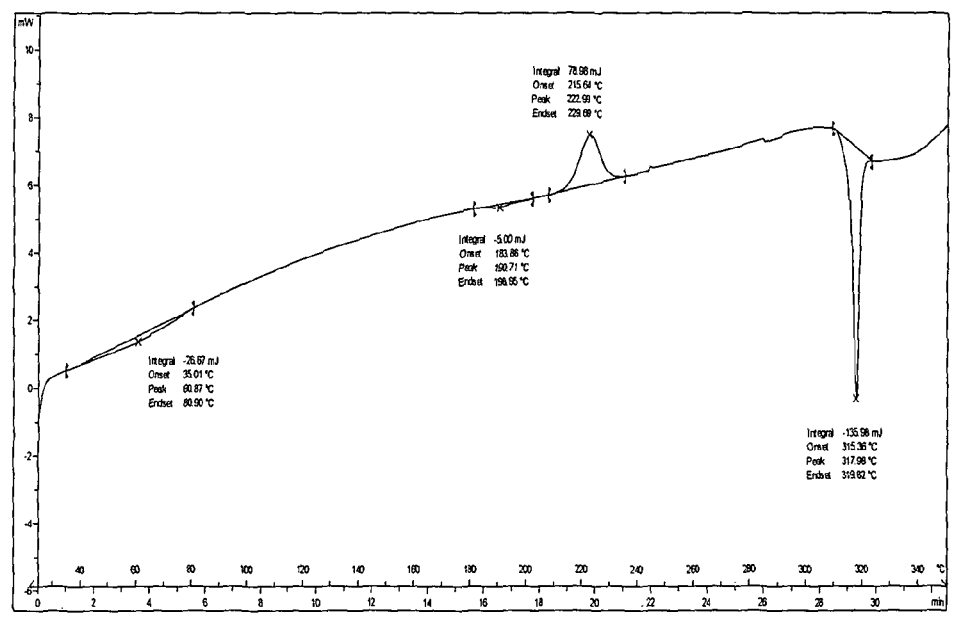

FIG. 14: DSC diffractogram of ivacaftor amorphous form I according to example 5.

Figure 15:
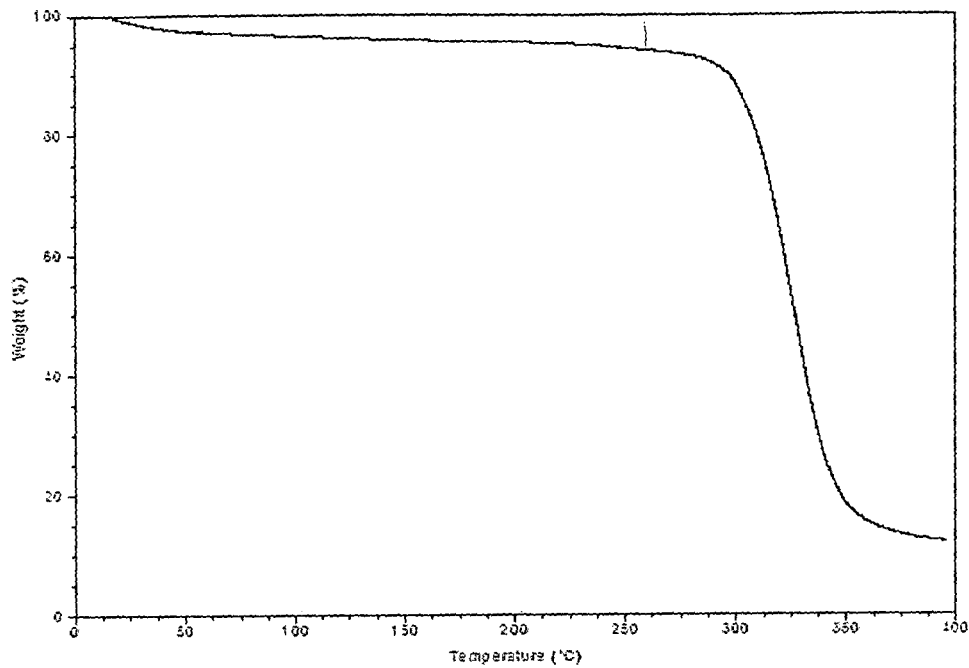

FIG. 15: TGA thermogram of ivacaftor amorphous form I according to example 5.

Figure 16:
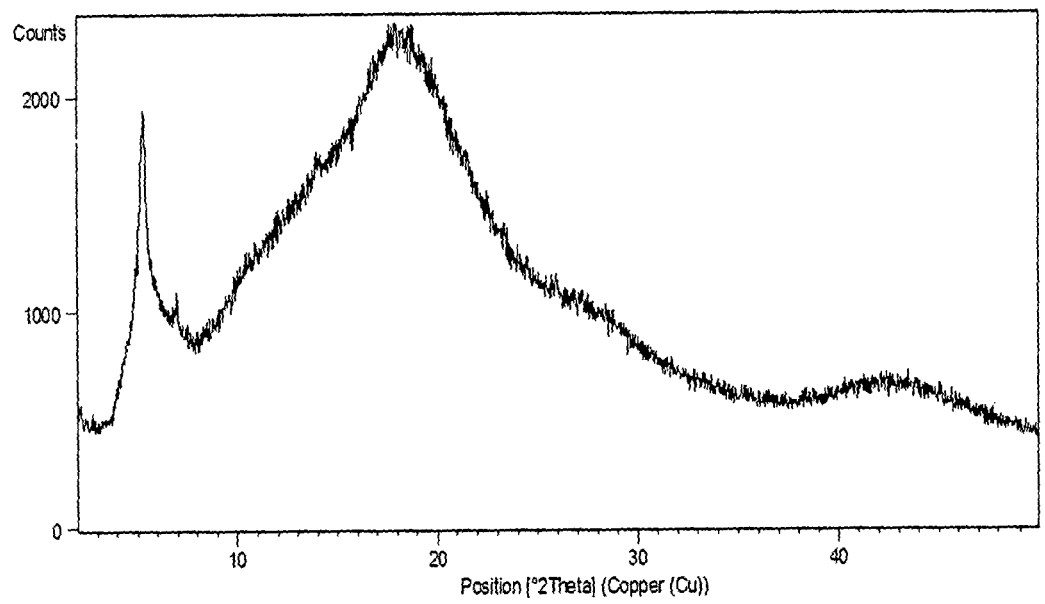

FIG. 16: XRD pattern of ivacaftor amorphous form II according to example 6.

Figure 17:
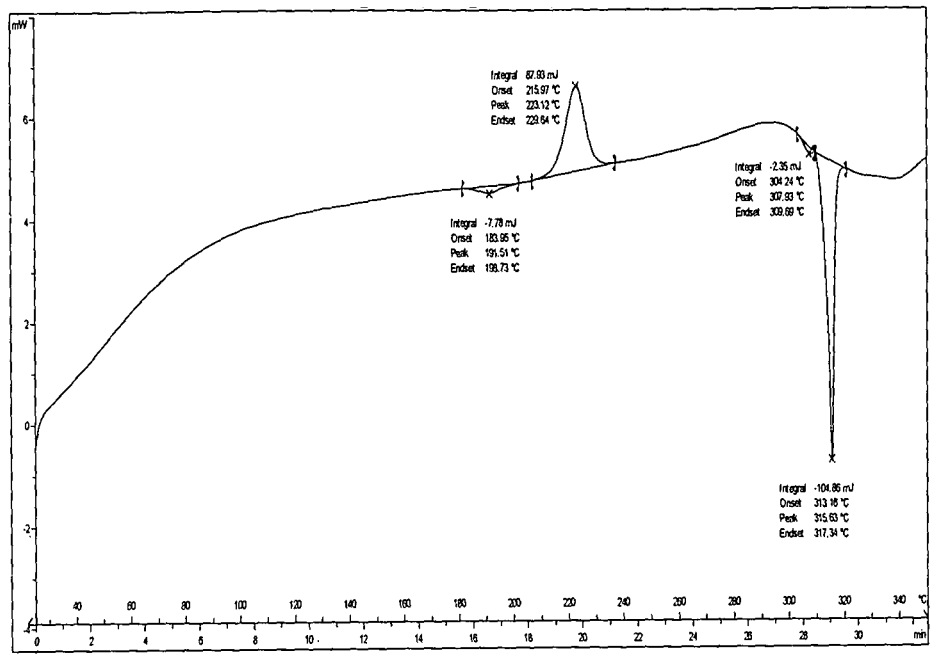

FIG. 17: DSC diffractogram of ivacaftor amorphous form II according to example 6.

Figure 18:
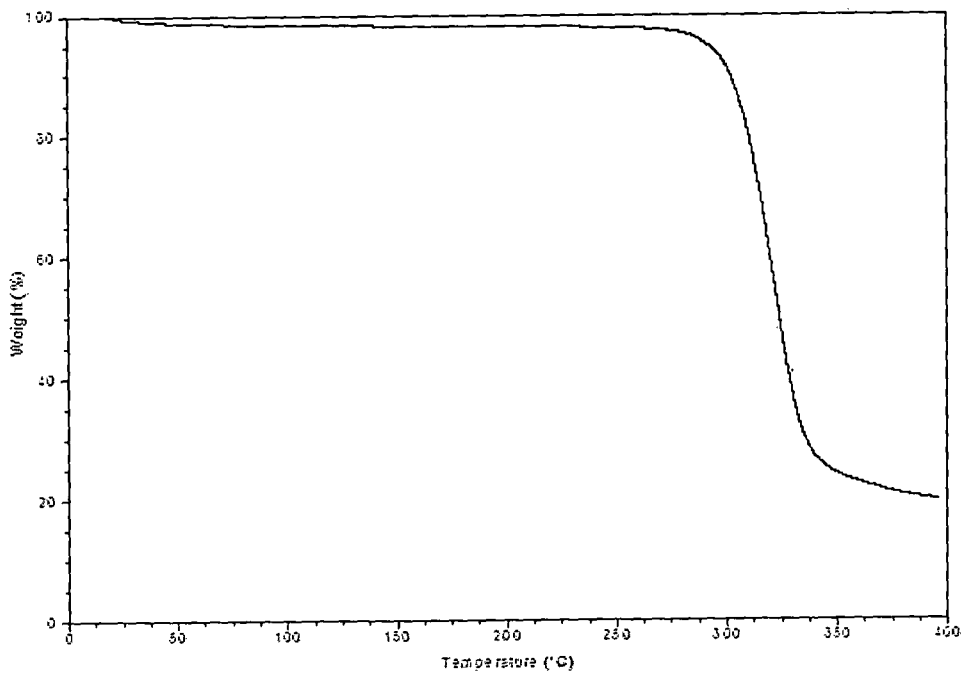

FIG. 18: TGA thermogram of ivacaftor amorphous form II according to example 6.

Figure 19:
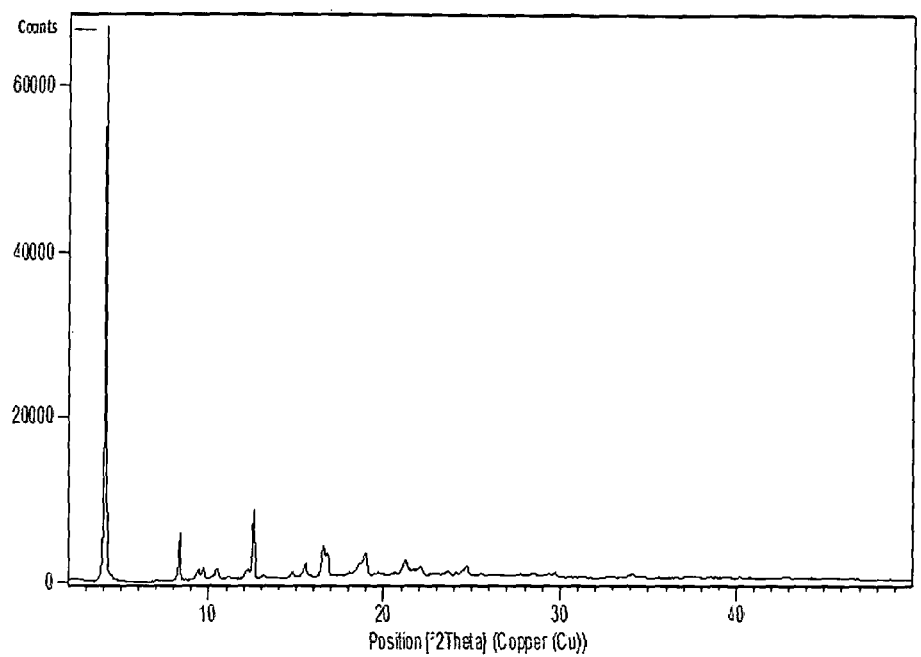

FIG. 19: XRD pattern of ivacaftor.propylene glycol solvate according to example 7.

Figure 20:
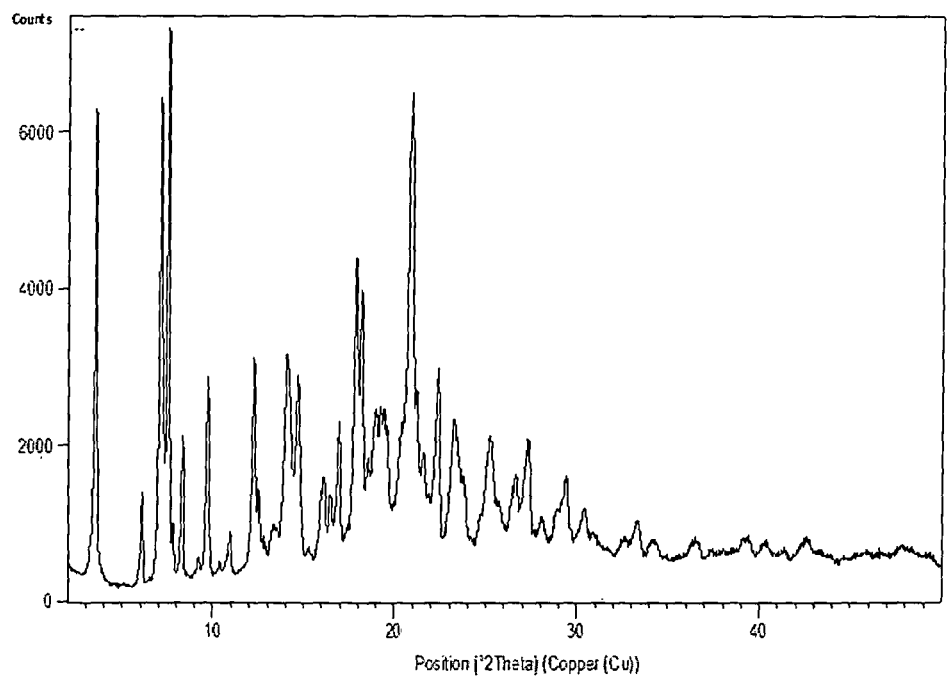

FIG. 20: XRD pattern of ivacaftor.DMF solvate according to example 8.

Figure 21:
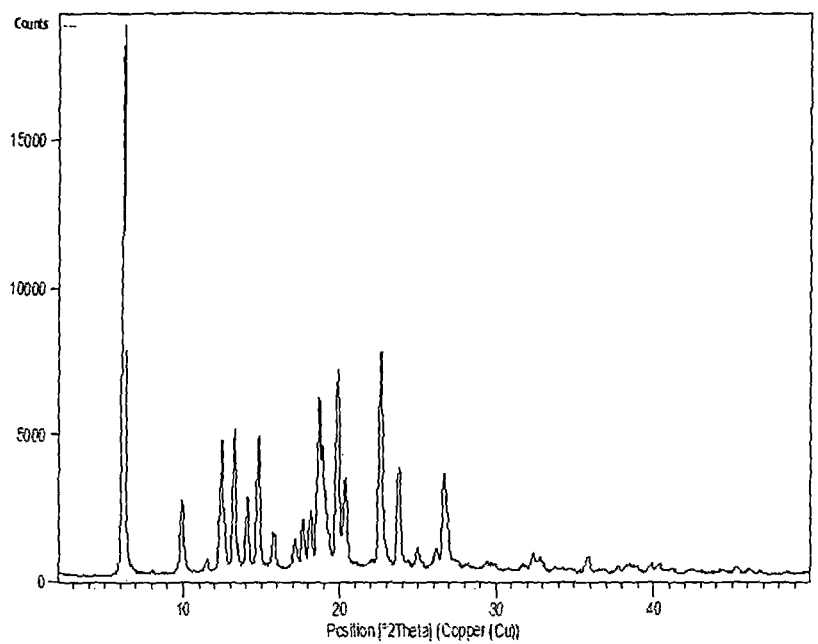

FIG. 21: XRD pattern of ivacaftor.THF solvate according to example 9.

Figure 22:
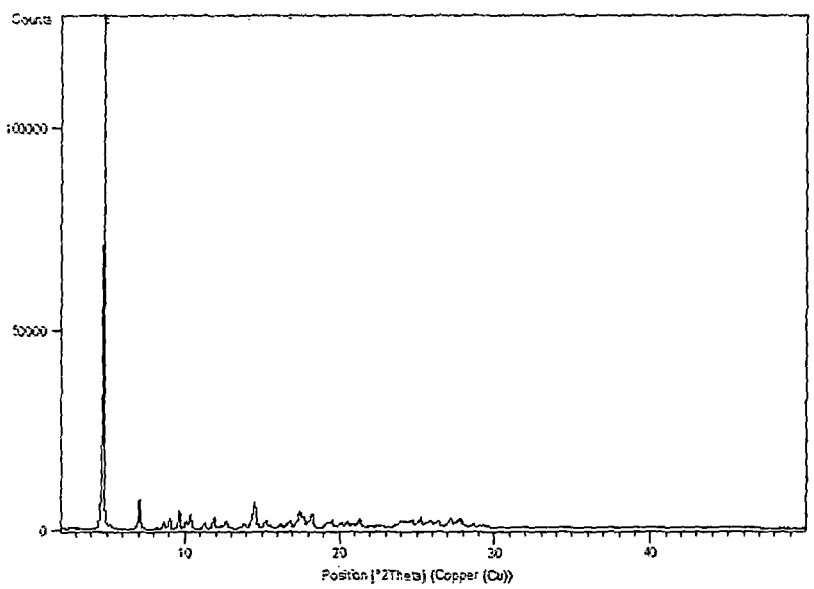

FIG. 22: XRD pattern of ivacaftor.DMF. ethyl actetate solvate according to example 10.

Figure 23:
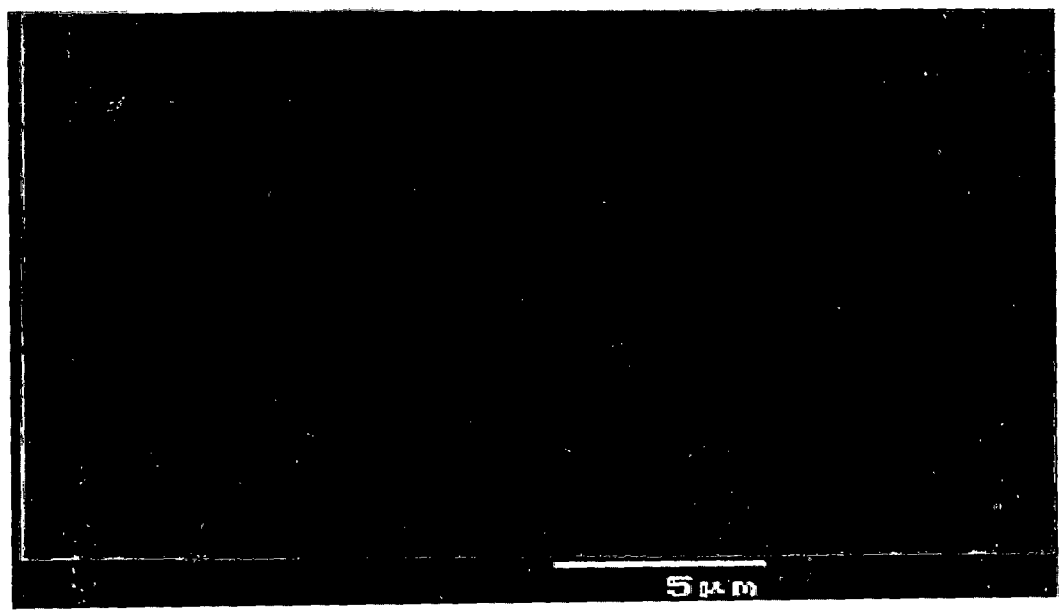

FIG. 23: Scanning electron micrograph (SEM) of crystalline ivacaftor Form G'.

Figure 24:
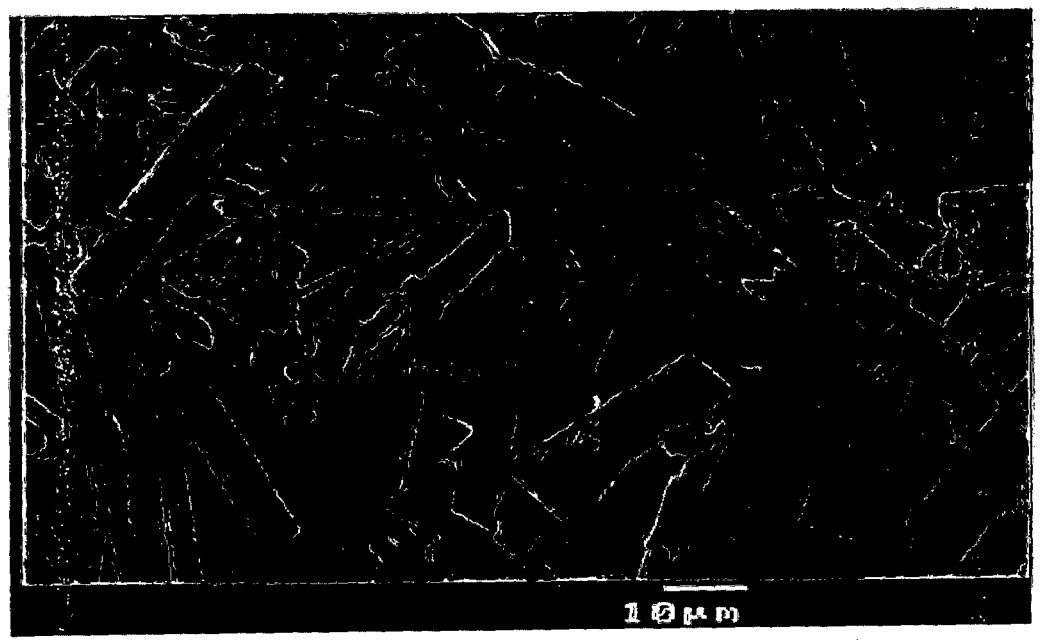

FIG. 24: Scanning electron micrograph (SEM) of crystalline ivacaftor.butanol solvate.

Figure 25:
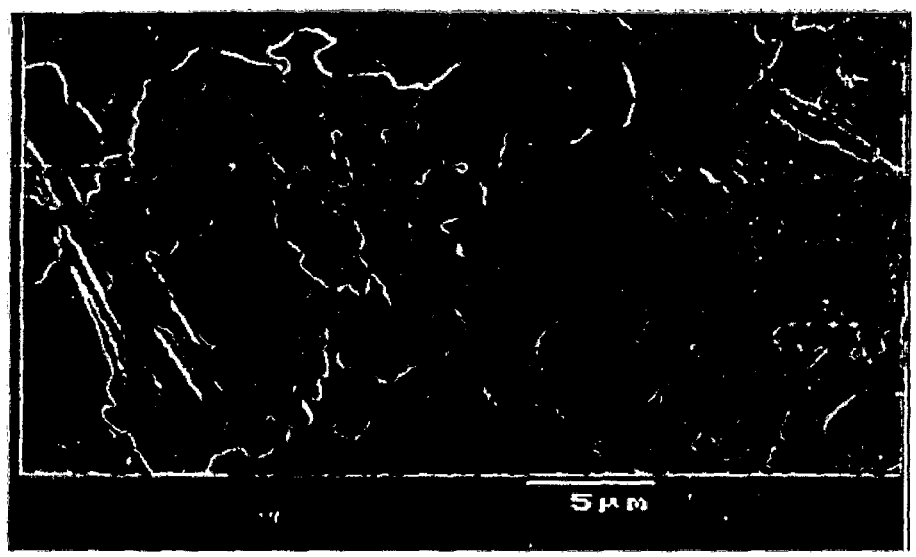

FIG. 25: Scanning electron micrograph (SEM) of crystalline ivacaftor.methanol solvate.

Figure 26:
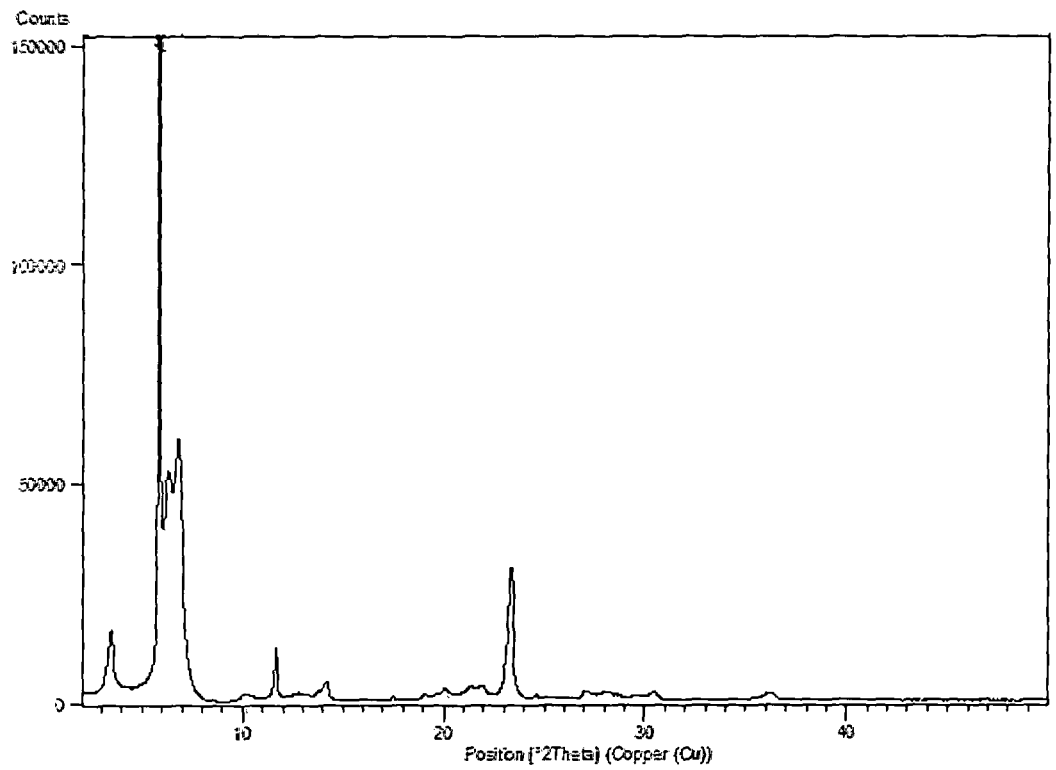

FIG. 26: XRD pattern of ivacaftor.n-butanol solvate, according to example 11

Figure 27:
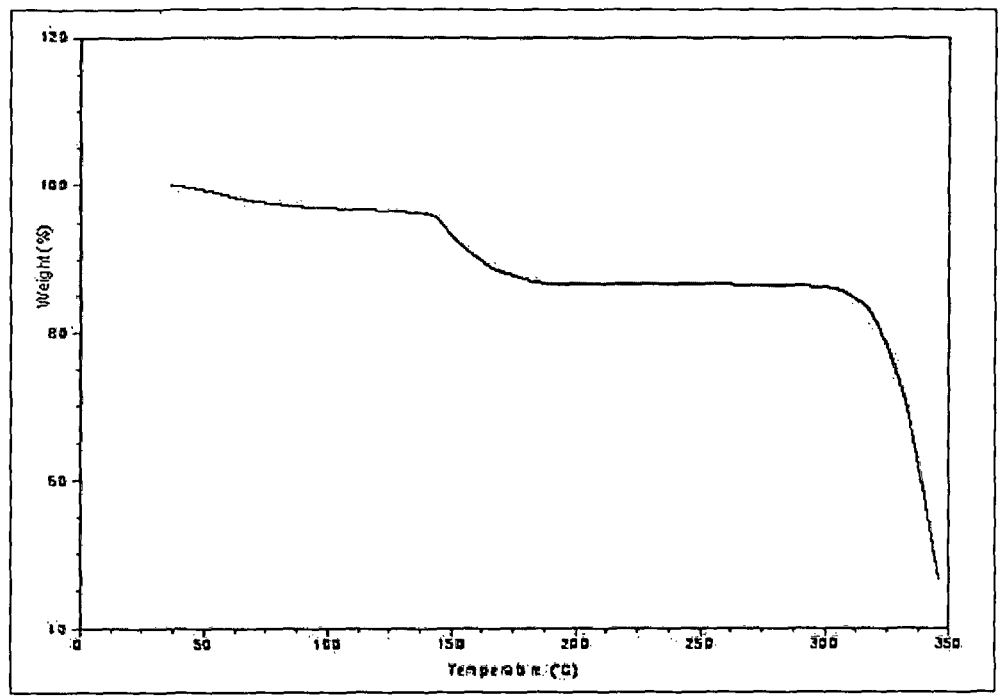

FIG. 27: TGA thermogram of ivacaftor.n-butanol solvate according to example 11

Figure 28:
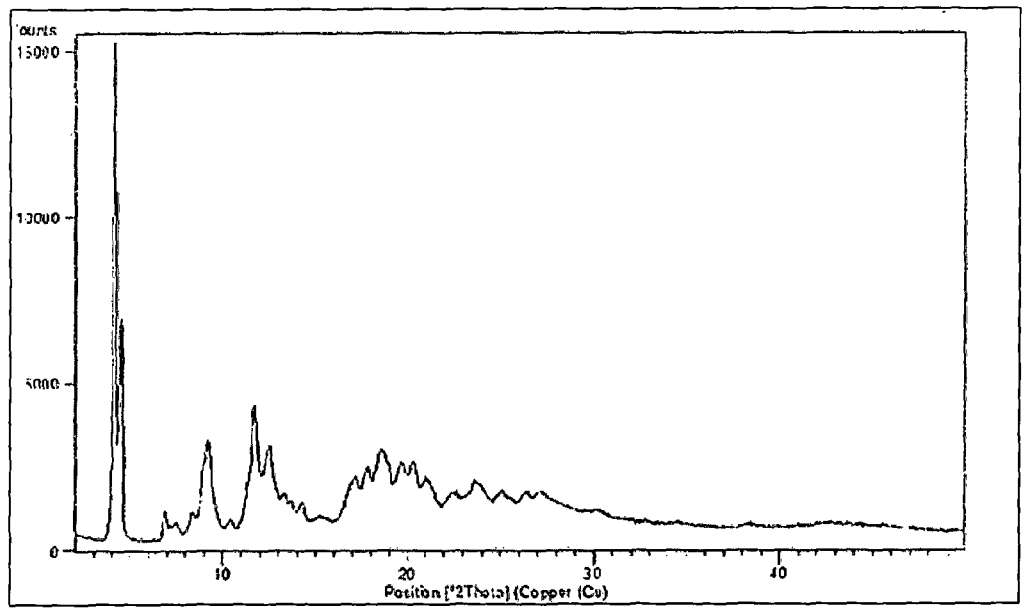

FIG. 28: XRD pattern of ivacaftor form D according to example 13

Figure 29:
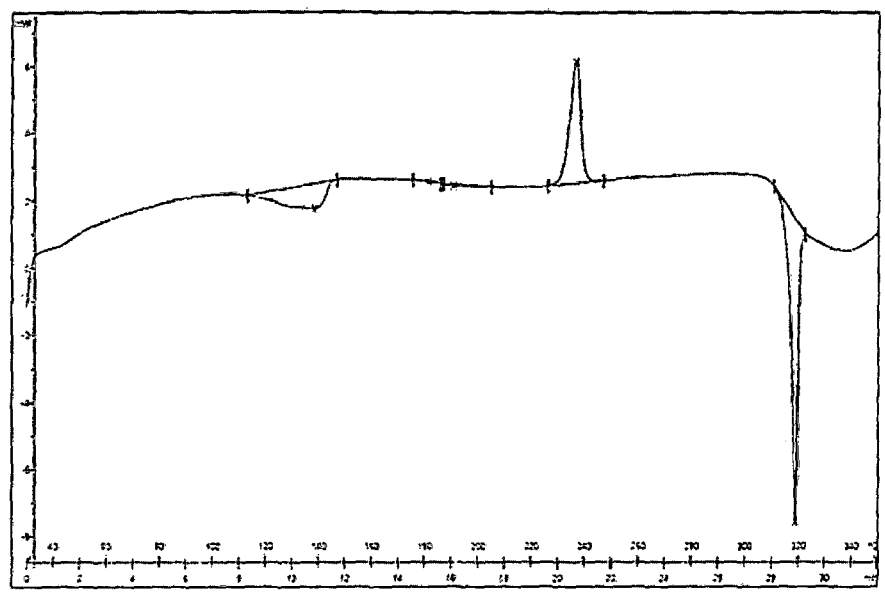

FIG. 29: DSC diffractogram of ivacaftor form D according to example 13

Figure 30:
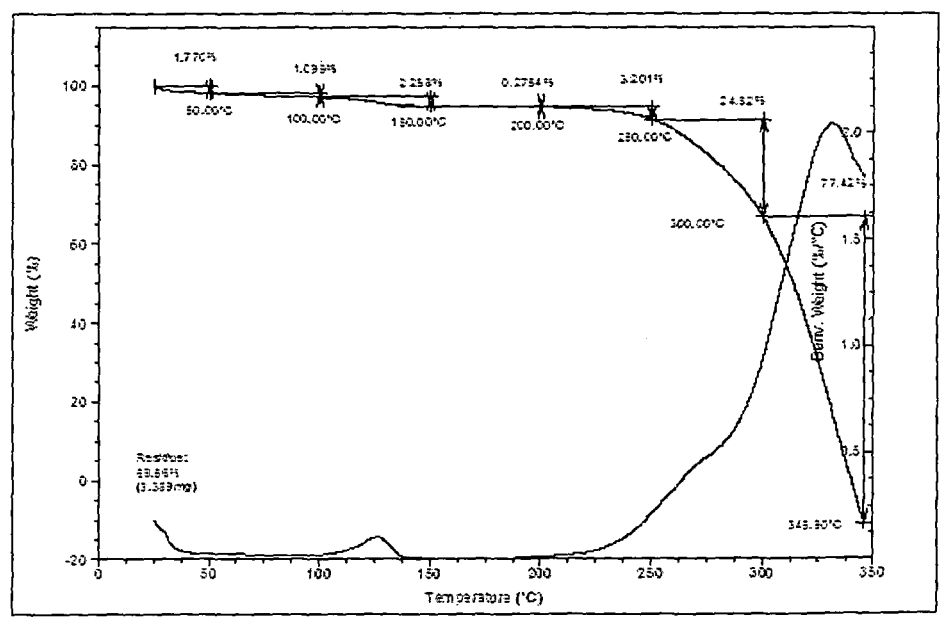

FIG. 30: TGA thermogram of ivacaftor form D according to example 13.

Figure 31:
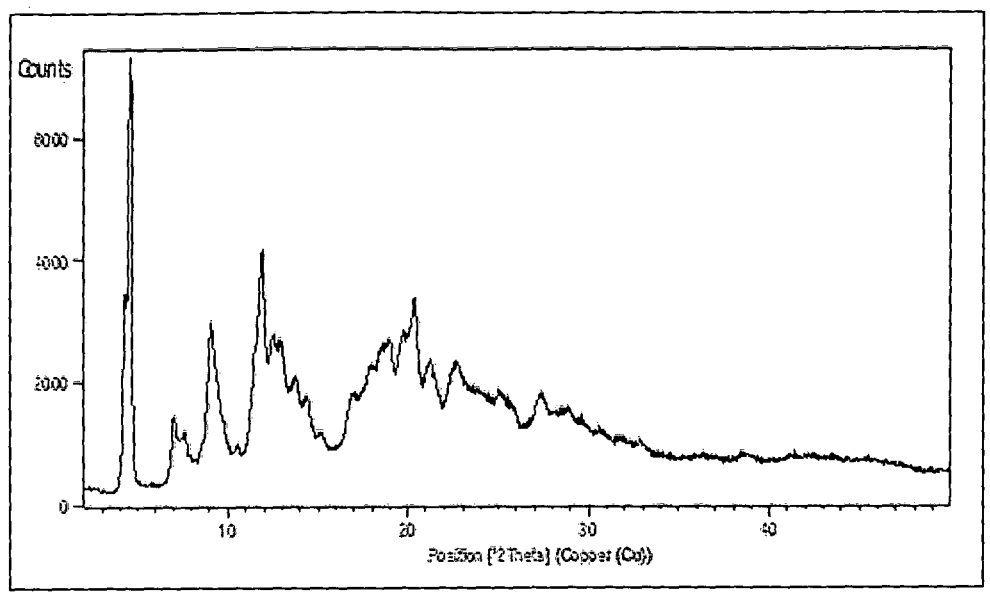

FIG. 31: XRD pattern of ivacaftor form E according to example 14

Figure 32:
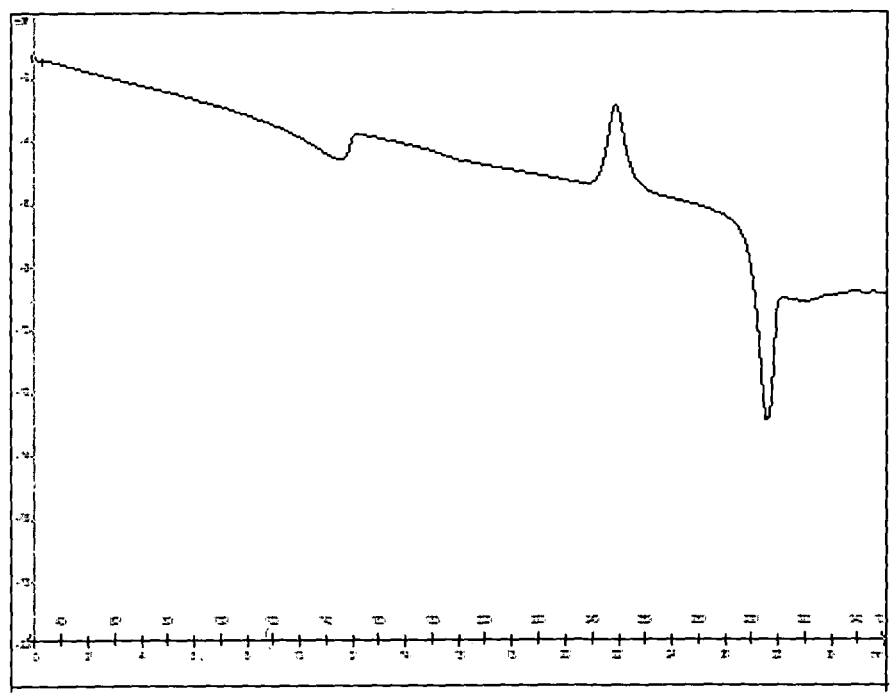

FIG. 32: DSC diffractogram of ivacaftor form E according to example 14

Figure 33:
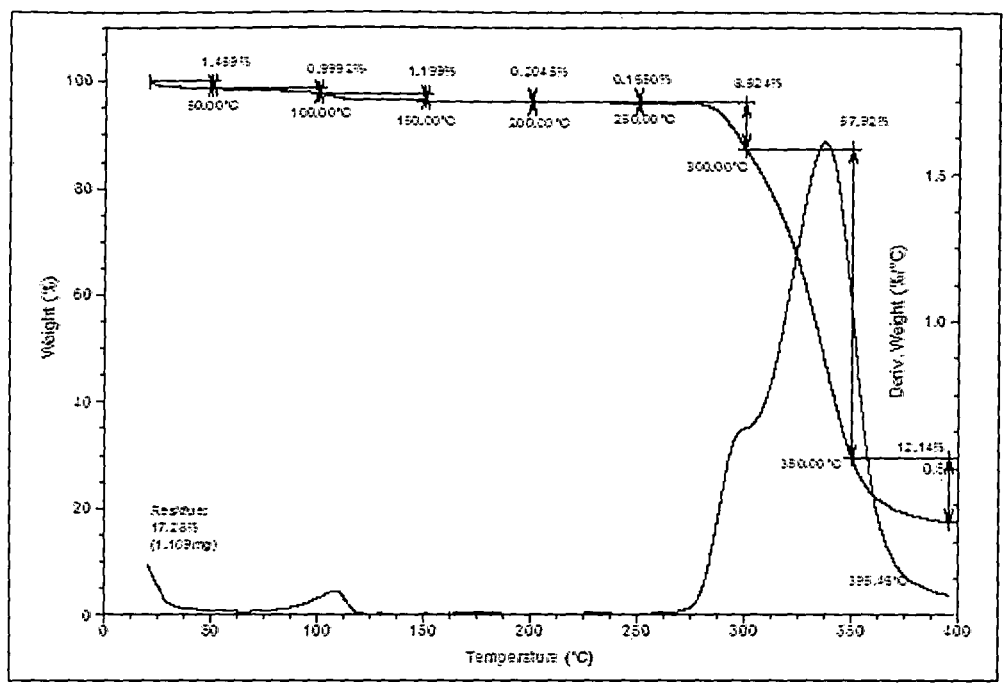

FIG. 33: TGA thermogram of ivacaftor form E according to example 14.

Figure 34:
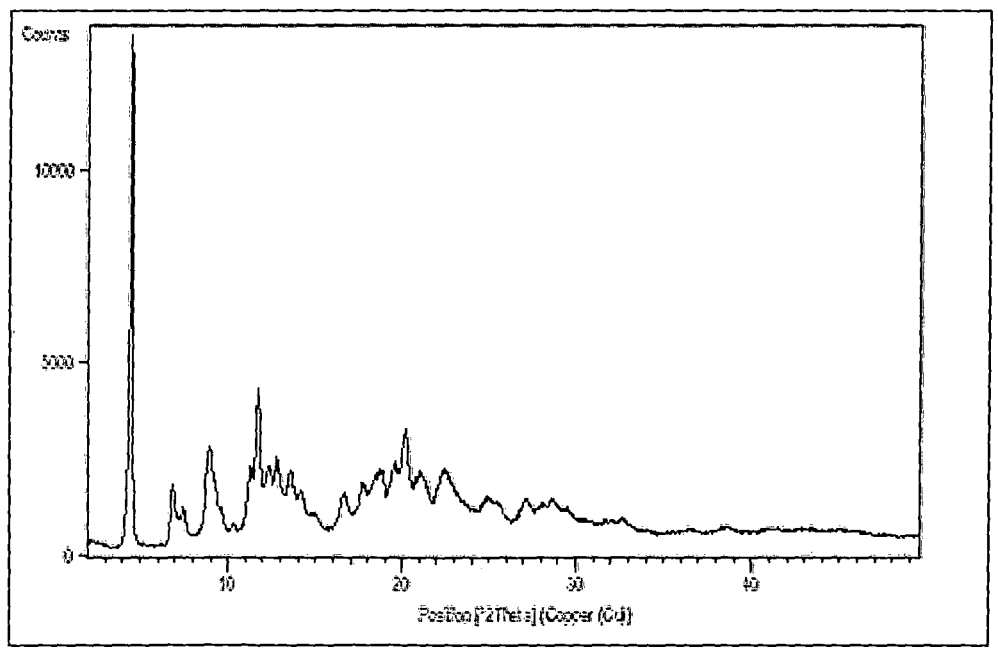

FIG. 34: XRD pattern of ivacaftor form E1 according to example 15

Figure 35:
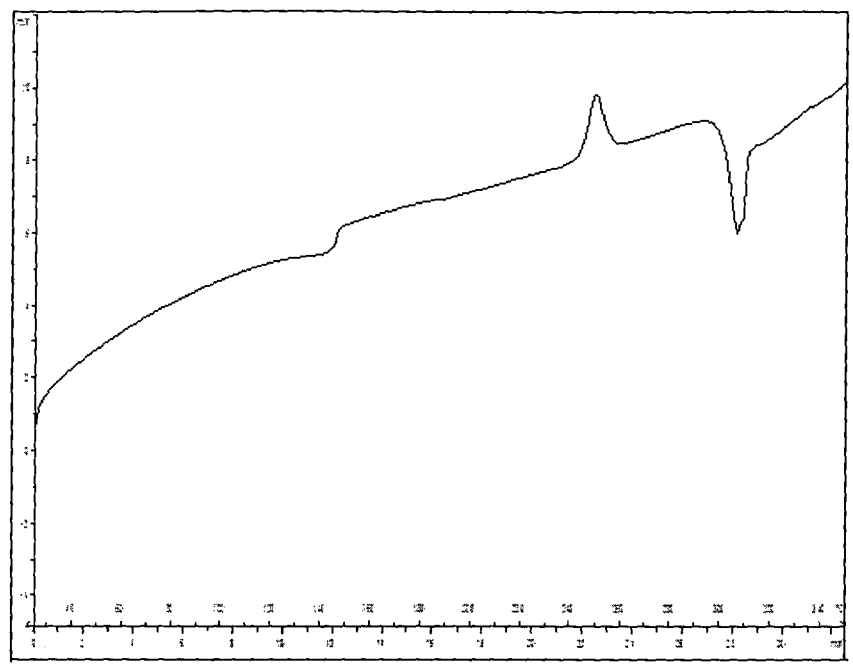

FIG. 35: DSC diffractogram of ivacaftor form E1 according to example 15

Figure 36:
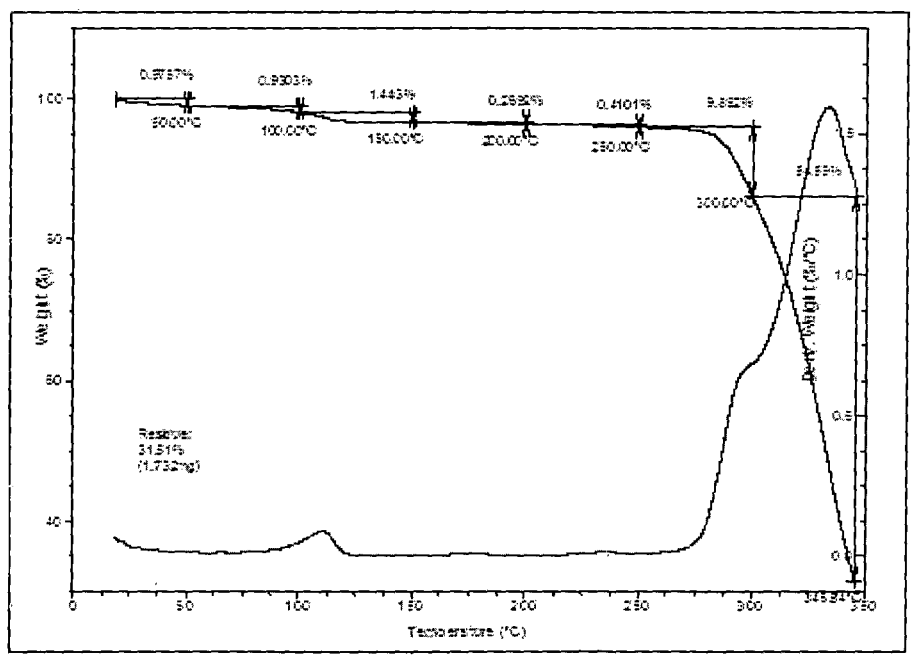

FIG. 36: TGA thermogram of ivacaftor form E1 according to example 15.

DETAILED DESCRIPTION OF THE
INVENTION

In one embodiment, the present invention provides crystalline ivacaftor.n-butanol solvate.

In one embodiment the present invention provides crystalline ivacaftor.n-butanol solvate characterized by X-ray diffraction (XRD) spectrum having peak reflections at about 3.4 and 14.2±0.2 degrees 2 theta.

In one embodiment the present invention provides crystalline ivacaftor.n-butanol solvate characterized by X-ray diffraction (XRD) spectrum having peak reflections at about 5.8, 6.8 and 23.3±0.2 degrees 2 theta.

In one embodiment the present invention provides crystalline ivacaftor.n-butanol solvate characterized by X-ray diffraction (XRD) spectrum having peak reflections at about 3.4, 5.8, 6.8 14.2 and 23.3±0.2 degrees 2 theta.

In one embodiment the present invention provides crystalline ivacaftor.n-butanol solvate characterized by X-ray diffraction (XRD) spectrum having peak reflections at about 3.4, 5.8, 6.8 14.2 and 23.3±0.2 degrees 2 theta which is substantially in accordance with FIG. 26.

In one embodiment, the present invention provides crystalline ivacaftor.n-butanol solvate characterized by Thermogravimetric Analysis (TGA) thermogram, showing a weight loss of about 10.5 to 13.5% at 185° C. determined over the temperature range of 0° C. to 400° C. and heating rate 10° C./min.

In one embodiment, the present invention provides crystalline ivacaftor.n-butanol solvate characterized by Thermogravimetric Analysis (TGA) thermogram, showing a weight loss of about 10.5 to 13.5% at 185° C. determined over the temperature range of 0° C. to 400° C. and heating rate 10° C./min which is in accordance with FIG. 27.

In one embodiment the present invention provides crystalline ivacaftor.n-butanol solvate characterized by X-ray diffraction (XRD) spectrum having peak reflections at about 3.4 and 14.2±0.2 degrees 2 theta which is in accordance with FIG. 26 and TGA thermogram, showing a weight loss of 10.5 to 13.5% at 185° C. determined over the temperature range of 0° C. to 400° C. and heating rate 10° C./min which is in accordance with FIG. 27.

In one embodiment, the present invention provides a process for the preparation of crystalline ivacaftor.n-butanol solvate comprising:
a) treating ivacaftor or a solvate thereof with n-butanol to obtain a mixture;
b) optionally, heating the above mixture of step 'a';
c) cooling the above mixture of step 'b,'; and
d) isolating crystalline ivacaftor.n-butanol solvate.

As used herein the term "treating" refers to contacting, suspending or slurrying.

In one embodiment, in step a) of the above process ivacaftor or a solvate thereof is treated with n-butanol to obtain a mixture.

In one embodiment, the solvate may be selected from methanol, ethanol, isopropanol, ethylacetate, tetrahydrofuran and the like. Preferably, the solvate is methanol.

In one embodiment, in step b) of the above process the mixture is heated to a temperature of about 65 to about 100° C. to obtain a solution. Preferably, the mixture is heated to a temperature of about 80 to about 85° C.

In one embodiment, in step c) of the above process the solution of solvate of ivacaftor in n-butanol is cooled to a temperature of about 25 to about 30° C.

In one embodiment, in step d) of the above process the crystalline ivacaftor.n-butanol solvate is isolated by methods known in the art such as filtration, centrifugation and the like.

In one embodiment, the present invention provides a process for the preparation of the crystalline ivacaftor.n-butanol solvate comprising treating the crystalline ivacaftor.methanol solvate with n-butanol to obtain a reaction mixture. The reaction was heated to a temperature of about 80 to about 85° C. the solution of crystalline ivacaftor.methanol solvate in n-butanol was maintained for a period of about 15 min to about 2 hours. Preferably, the reaction mixture is maintained for a period of about 30 min. The reaction mixture is then cooled to a temperature of about 25 to about 30° C.

In one embodiment, the present invention provides a process for the preparation of crystalline ivacaftor.n-butanol solvate comprising isolating crystalline ivacaftor.n-butanol solvate from an n-butanol solution.

In one embodiment, the present invention provides a process for the preparation of crystalline ivacaftor.n-butanol solvate comprising mixing ivacaftor and n-butanol to form a solution and isolating the crystalline ivacaftor.n-butanol solvate from the solution.

In one embodiment, the crystalline ivacaftor.n-butanol solvate is isolated by dissolving ivacaftor in n-butanol to form a solution at elevated temperature followed by cooling the solution and isolating ivacaftor.n-butanol solvate.

In one embodiment, the crystalline ivacaftor.n-butanol solvate is isolated by dissolving ivacaftor in a mixture of n-butanol and acetonitrile to form a solution at elevated temperature followed by cooling the solution and isolating ivacaftor.n-butanol solvate.

In one embodiment, the present invention provides a process for the preparation of crystalline ivacaftor.n-butanol solvate characterised by X-ray diffraction (XRD) spectrum having peak reflections at about 3.4 and 14.2±0.2 degrees 2 theta comprising drying crystalline ivacaftor.n-butanol solvate obtained by any of the processes disclosed above for a period of about 5 to about 120 hours.

In one embodiment, the present invention provides a process for the preparation of crystalline ivacaftor.n-butanol solvate characterised by X-ray diffraction (XRD) spectrum having peak reflections at about 3.4 and 14.2±0.2 degrees 2 theta comprising drying crystalline ivacaftor.n-butanol solvate obtained by any of the processes disclosed above for a period of about 20 to about 80 hours. Preferably, for a period of about 50 to about 70 hours.

In one embodiment, the present invention provides a process for the preparation of crystalline ivacaftor.n-butanol solvate characterised by X-ray diffraction (XRD) spectrum having peak reflections at about 3.4 and 14.2±0.2 degrees 2 theta and having a ratio of ivacaftor:n-butanol of 1:0.5 to 1:1. Preferably having a ratio of ivacaftor to n-butanol of 1:0.7. In one embodiment, the crystalline ivacaftor.n-butanol solvate obtained has an n-butanol content in the range of about 79423 to 125000. Preferably, crystalline ivacaftor.n-butanol solvate obtained has an n-butanol content of 111475 ppm as analysed by GC (Gas chromatography):

In one embodiment, the present invention provides crystalline ivacaftor.n-butanol solvate peak reflections at about 3.4 and 14.2±0.2 degrees 2 theta wherein the crystalline ivacaftor.n-butanol solvate has been dried for a period of about 60 hours and has a butanol content of about 111475 ppm as analysed by GC.

In one embodiment the present invention provides crystalline ivacaftor.n-butanol solvate characterized by X-ray diffraction (XRD) spectrum having peak reflections at about 5.91, 6.37, 10.53, 20.19 and 23.57±0.2 degrees 2 theta.

In one embodiment the present invention provides crystalline ivacaftor.n-butanol solvate characterized by Differential Scanning calorimetric (DSC) thermogram having endothermic peak at about 315.25, 184.91, 156.06, 150.74 and 103.25±1° C. and exothermic peak at 231.68±1° C.

In one embodiment the present invention provides crystalline ivacaftor.n-butanol solvate characterized by X-ray diffraction (XRD) spectrum having peak reflections at about 5.91, 6.37, 10.53, 20.19 and 23.57±0.2 degrees 2 theta and Differential Scanning calorimetric (DSC) thermogram having endothermic peak at about 315.25, 184.91, 156.06, 150.74 and 103.25±1° C. and exothermic peak at 231.68±1° C.

In one embodiment the present invention provides crystalline ivacaftor.n-butanol solvate characterized by X-ray diffraction (XRD) spectrum having peak reflections at about 5.91, 6.37, 10.53, 20.19 and 23.57±0.2 degrees 2 theta which is substantially in accordance with FIG. 4 and Differential Scanning calorimetric (DSC) thermogram having endothermic peak at about 315.25, 184.91, 156.06, 150.74 and 103.25±1° C. and exothermic peak at 231.68±1° C. which is substantially in accordance with FIG. 5.

In one embodiment, the present invention provides crystalline ivacaftor.n-butanol solvate characterized by Thermogravimetric Analysis (TGA) thermogram, showing a weight loss of about 19.1% at 185° C. determined over the temperature range of 0° C. to 400° C. and heating rate 10° C./min.

In one embodiment, the present invention provides crystalline ivacaftor.n-butanol solvate characterized by Thermogravimetric Analysis (TGA) thermogram, which is substantially in accordance with FIG. 6.

In one embodiment the present invention provides crystalline ivacaftor.n-butanol solvate characterized by X-ray diffraction (XRD) spectrum having peak reflections at about 5.91, 6.37, 10.53, 20.19 and 23.57±0.2 degrees 2 theta and Thermogravimetric Analysis (TGA) thermogram, showing a weight loss of about 19.1% at 185° C. determined over the temperature range of 0° C. to 400° C. and heating rate 10° C./min.

In one embodiment, the present invention provides crystalline ivacaftor.n-butanol solvate having a cylindrical morphology as observed by SEM, which is substantially in accordance with FIG. 24.

In one embodiment, the present invention provides a process for the preparation of crystalline ivacaftor.n-butanol solvate characterised by X-ray diffraction (XRD) spectrum having peak reflections at about 5.91, 6.37, 10.53, 20.19 and 23.57±0.2 degrees 2 theta comprising drying crystalline ivacaftor.n-butanol solvate obtained by any of the processes disclosed above for a period of about 1 hour to about 4 hours. Preferably, the solvate is dried for a period of about 2 hours.

In one embodiment, the crystalline ivacaftor.n-butanol solvate has a butanol content in the range of about 131000 to about 200000. Preferably, the butanol content is 136000.

In one embodiment, the present invention provides a process for the preparation of crystalline ivacaftor.n-butanol solvate characterised by X-ray diffraction (XRD) spectrum having peak reflections at about 5.91, 6.37, 10.53, 20.19 and 23.57±0.2 degrees 2 theta comprising drying crystalline ivacaftor.n-butanol solvate obtained by any of the processes disclosed above for a period of about 1 hour to about 10 hours. Preferably, the solvate is dried for a period of about 2 hours and has a butanol content of about 136000 ppm.

In one embodiment, the present invention provides crystalline ivacaftor.n-butanol solvate having a ratio ivacaftor: n-butanol of 1:0.4.

In one embodiment, the present invention provides crystalline ivacaftor.n-butanol solvate having a ratio ivacaftor: n-butanol of 1:0.8 to 1:1.3 preferably 1:1.25.

In one embodiment, the present invention provides crystalline ivacaftor.methanol solvate.

In one embodiment the present invention provides crystalline ivacaftor.methanol solvate characterized by X-ray diffraction (XRD) spectrum having peak reflections at about 7.28, 13.84, 14.03, 19.78, 20.27 and 20.92±0.2 degrees 2 theta.

In one embodiment, the present invention provides crystalline ivacaftor.methanol solvate characterised by Differential Scanning calorimetric (DSC) thermogram having endothermic peak at about 320.88 and 192.13±1° C. and exothermic peak at about 245.63±1° C.

In one embodiment the present invention provides crystalline ivacaftor.methanol solvate characterized by X-ray diffraction (XRD) spectrum having peak reflections at about 7.28, 13.84, 14.03, 19.78, 20.27 and 20.92±0.2, which is substantially in accordance with FIG. 7 and Differential Scanning calorimetric (DSC) thermogram having endothermic peak at about 320.88 and 192.13±1° C. and exothermic peak at about 245.63±1° C., which is substantially in accordance with FIG. 8.

In one embodiment, the present invention provides crystalline ivacaftor methanol.solvate characterized by Thermogravimetric Analysis (TGA) thermogram, showing a weight loss of about 7.94% at 185° C. determined over the temperature range of 0° C. to 400° C. and heating rate of 10° C./min.

In one embodiment, the present invention provides crystalline ivacaftor.methanol solvate characterized by Thermogravimetric Analysis (TGA) thermogram, which is substantially in accordance with FIG. 9.

In one embodiment, the present invention provides crystalline ivacaftor.methanol solvate having a irregular morphology as observed by SEM, which is substantially in accordance with FIG. 25.

In one embodiment, the present invention provides a process for the preparation of crystalline ivacaftor.methanol solvate comprising:
a) treating ivacaftor with methanol to obtain a mixture;
b) optionally, heating the above mixture of step 'a';
c) cooling the above mixture of step 'b'; and
d) isolating crystalline ivacaftor.methanol solvate.

In one embodiment, in step a) of the above process ivacaftor is treated with methanol to obtain a mixture.

In one embodiment, in step b) of the above step the mixture is heated to a temperature of about 30 to about reflux temperature for a period of about 20 to 40 hours.

In one embodiment, the mixture of ivacaftor in methanol is heated to reflux temperature and maintained for a period of about 25 to 30 hours.

In one embodiment, in step c) of the above process the mixture of ivacaftor in methanol is cooled to a temperature of about 0-30° C. Preferably, the mixture is cooled to about 25 to 30° C.

In one embodiment, in step d) of the above process the crystalline ivacaftor.methanol solvate is isolated by methods known ion the art such as filtration, centrifugation and the like.

In one embodiment, the present invention provides a process for the preparation of crystalline ivacaftor.methanol solvate comprising isolating ivacaftor methanol.solvate from a methanol solution.

In one embodiment, the present invention provides a process for the preparation of crystalline ivacaftor.methanol solvate comprising adding methanol to ivacaftor obtained by reacting 4-oxo-1,4-dihydroquinoline-3-carboxylic acid, a compound of formula XI and 5-amino-2,4-di-tert-butyl phenol, a compound of formula II. The reaction mixture containing ivacaftor and methanol is heated to a temperature of about 55-75° C. Preferably, the mixture is heated to a temperature of about 60-65° C. followed by cooling the solution.

In one embodiment, the present invention provides crystalline ivacaftor.methanol solvate having a ratio of 1:1.

In one embodiment, the present invention provides a process for the preparation of ivacaftor, a compound of formula I, in amorphous form, the process comprising:
(a) dissolving a solvate of ivacaftor in a solvent to form a solution; and
(b) removing the solvent from the solution obtained in (a).

In one embodiment, in step a) of the above process the solvate of ivacaftor is solvate with methanol, isopropanol, n-butanol, ethyl acetate, tetrahydrofuran, dimethyl formamide or mixtures thereof. Preferably, the solvate is n-butanol solvate.

In one embodiment, in step a) of the above process the solvate of ivacaftor is dissolved in a solvent is selected from the group consisting of water, ketone such as acetone, methyl ethyl ketone, and alcohols like isopropyl alcohol, n-butanol, isobutanol and the like or mixtures thereof). Preferably the solvent is a mixture of methyl ethyl ketone and water. Preferably, the solvent is a mixture of methyl ethyl ketone and water.

In one embodiment, in step b) of the above process the solvent is removed by spray drying, fluid bed drying, lyophilization, flash drying, spin flash drying, or thin-film drying.

In one embodiment, the present invention provides a process for the preparation of ivacaftor, the compound of formula I, in amorphous form, from a solvate of ivacaftor wherein the solvate is crystalline ivacaftor.n-butanol solvate.

In one embodiment, the present invention provides a process for the preparation of ivacaftor.n-butanol solvate, the process comprising;
a) converting ivacaftor, the compound of formula I to crystalline ivacaftor.methanol solvate; and
b) converting crystalline ivacaftor.methanol solvate to crystalline ivacaftor.n-butanol solvate.

In one embodiment, in step a) of the above process ivacaftor is dissolved in methanol to obtain a mixture. The mixture is heated to reflux temperature and maintained for a period of about 25 to about 30° C. The mixture is cooled to a temperature of 25 to about 30° C. and crystalline ivacaftor.methanol solvate is isolated by methods known the art such as filtration, centrifugation and the like.

In one embodiment, in step b) of the above process crystalline ivacaftor.methanol solvate is converted to crystalline ivacaftor.n-butanol solvate by a process comprising dissolving the crystalline ivacaftor.methanol solvate in n-butanol.

In one embodiment, the solution of crystalline ivacaftor.methanol solvate is obtained by heating a mixture of crystalline ivacaftor.methanol solvate in n-butanol to a temperature of about 65 to about 100° C.

In one embodiment, the solution of crystalline ivacaftor.methanol solvate in n-butanol is maintained at a temperature of about 85 to about 90° C. for a period of about 15 min to about 2 hours. Preferably, the solution is maintained for a period of about 30 minutes.

In one embodiment, the solution is cooled to a temperature of about 20-30° C. Preferably) the solution is cooled to a temperature of about 25-30° C.

In one embodiment, crystalline ivacaftor.n-butanol solvate is isolated by methods known in the art such as filtration, centrifugation and the like.

In one embodiment, the crystalline ivacaftor.n-butanol solvate is dissolved in a mixture of methyl ethyl ketone and water and subjected to spray drying.

In one embodiment, the spray drying is carried out with an inlet temperature of 85-95° C. and an outlet temperature of 65-75° C.

In one embodiment, the present invention provides amorphous ivacaftor, obtained by the process described herein above wherein, the compound of formula XII or XIII is less than 0.1% w/w of amorphous ivacaftor, as measured by HPLC (high performance liquid chromatography).

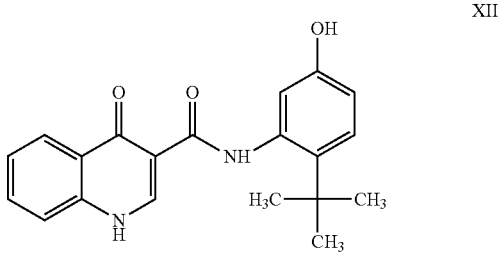

XII

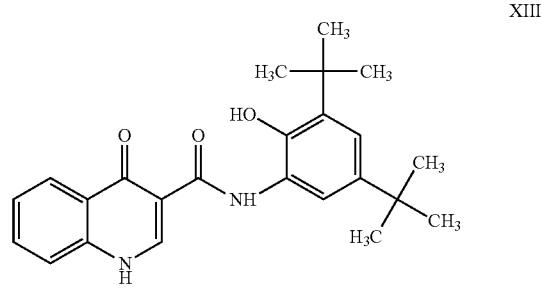

XIII

In one embodiment, the present invention provides amorphous ivacaftor, obtained by the process described herein above, free from the listed genotoxic impurities, compounds of formula XI, II, VIII, XIV, VII, XV and XVI.

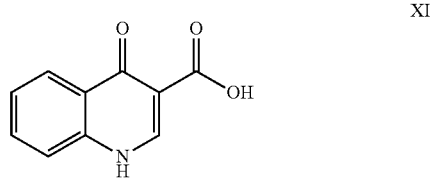

XI

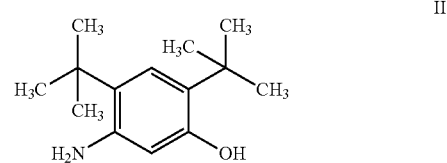 [SMILES: CC(C)(C)c1cc(C(C)(C)C)c(O)cc1N]

II

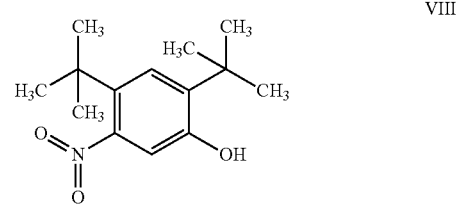

VIII

-continued

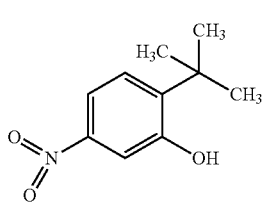
XIV

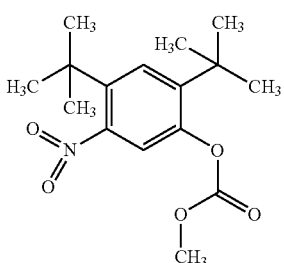
VII

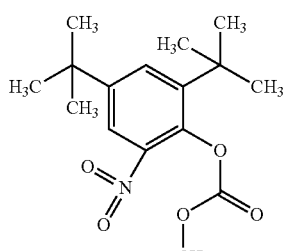
XV

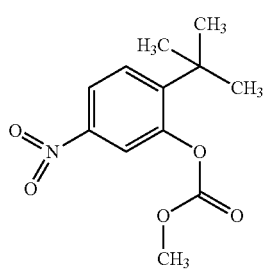
XVI

In one embodiment, the present invention provides amorphous ivacaftor free of genotoxic impurities, compounds of formula XI, II, VIII, XIV, VII, XV and XVI.

In one embodiment, the present invention provides crystalline ivacaftor Form G'.

In one embodiment, the present invention provides crystalline ivacaftor Form G' characterized by X-ray Diffraction (XRD) spectrum having peak reflections at about 4.98, 7.62, 10.57, 14.31 and 20.68.±0.2 degrees 2 theta.

In one embodiment, the present invention provides crystalline ivacaftor Form G' characterized by Differential Scanning calorimetric (DSC) thermogram having endothermic peak at about 186.77 and 318.08±1° C. and an exothermic peak at about 221.87±1° C.

In one embodiment, the present invention provides crystalline ivacaftor Form G' characterized by Thermogravimetric Analysis (TGA) thermogram, showing a weight loss of about 1.73% at 185° C. determined over the temperature range of 0° C. to 400° C. and heating rate of 10° C./min.

In one embodiment, the present invention provides ivacaftor Form G' characterized by X-ray Diffraction (XRD) spectrum having peak reflections at about 4.98, 7.62, 10.57, 14.31 and 20.68±0.2 degrees 2 theta which is substantially in accordance with FIG. 1, and Differential Scanning calorimetric (DSC) thermogram having endothermic peak at about 186.77 and 318.08±1° C. and an exothermic peak at 221.87±1° C. which substantially in accordance with FIG. 2.

In one embodiment, the present invention provides crystalline ivacaftor Form G' characterized by Thermogravimetric Analysis (TGA) thermogram, which is substantially: in accordance with FIG. 3.

In one embodiment, the present invention provides crystalline ivacaftor Form G' having water content in the range of 1.5-3% as measured by Karl Fischer.

In one embodiment, the present invention provides crystalline ivacaftor Form G' having water content in the range of 2.1-2.5% as measured by Karl Fischer.

In one embodiment, the present invention provides crystalline ivacaftor Form G' having water content of about 2.29% as measured by Karl Fischer.

In one embodiment, the present invention provides crystalline ivacaftor Form G' hemihydrate.

In one embodiment, the present invention provides crystalline ivacaftor Form G' having a discoidal morphology as observed by SEM (scanning electron micrograph), which is substantially in accordance with FIG. 23.

In one embodiment, the present invention provides a process for the preparation of crystalline ivacaftor Form G' comprising:
a) dissolving ivacaftor in n-butanol to form a solution;
b) isolating the ivacaftor.n-butanol solvate from the solution; and
c) drying the ivacaftor.n-butanol solvate to obtain ivacaftor Form G'.

In one embodiment, the ivacaftor.n-butanol solvate is subjected to milling prior to the drying step.

The milling may be carried out by pulverization techniques such as crushing using mortar and pestle or jet milling. The obtained ivacaftor.n-butanol solvate with reduced particle size is then subjected to drying to obtain crystalline ivacaftor Form G'.

The drying of crystalline ivacaftor.n-butanol solvate may be carried out for a period of about 1 hour to about 150 hours. Preferably, the drying may be carried out over a period of about 10-90 hours to obtain ivacaftor Form G'.

In one embodiment, the present invention provides crystalline ivacaftor Form G' by suspending ivacaftor.n-butanol solvate in acetonitrile and isolating.

In one embodiment, the present invention provides crystalline ivacaftor Form G' by suspending ivacaftor.n-butanol solvate in water and isolating.

In one embodiment, the present invention provides crystalline ivacaftor form G' wherein the butanol content is less than 5000 ppm as analysed by GC (gas chromatography).

In one embodiment, the present invention provides crystalline ivacaftor.n-butanol solvate wherein the crystalline ivacaftor.n-butanol has been dried for a period of 80 hours and has a butanol content of about 1500 ppm as analysed by GC (gas chromatography).

In one embodiment, the present invention provides crystalline ivacaftor Form G.

In one embodiment, the present invention provides crystalline ivacaftor Form G characterized by X-ray diffraction (XRD) spectrum having peak reflections at about 5.34, 9.69, 10.72, 12.09, 18.15 and 25.69±0.2 degrees 2 theta.

In one embodiment, the present invention provides crystalline ivacaftor Form G characterized by Differential Scanning calorimetric (DSC) thermogram having endothermic peak at about 322.1 and 169.60±1° C. exothermic peak at about 240.4±1° C.

In one embodiment, the present invention provides crystalline ivacaftor Form G characterized by X-ray diffraction (XRD) spectrum having peak reflections at about 5.34, 9.69, 10.72, 12.09, 18.15 and 25.69±0.2 degrees 2 theta, which is substantially in accordance with FIG. 10 and Differential Scanning calorimetric (DSC) thermogram having endothermic peak at about 322.1 and 169.6±1° C. exothermic peak at about 240.4±1° C., which is substantially in accordance with FIG. 11.

In one embodiment, the present invention provides crystalline ivacaftor Form G characterized by Thermogravimetric Analysis (TGA) thermogram, showing a weight loss of about 15.4% at 185° C. determined over the temperature range of 0° C. to 400° C. and heating rate 10° C./min.

In one embodiment, the present invention provides crystalline ivacaftor Form G characterized by Thermogravimetric Analysis (TGA) thermogram, which is substantially in accordance with FIG. 12.

In one embodiment, the present invention provides a process for the preparation of crystalline ivacaftor Form G comprising adding a mixture of DMF (dimethyl formamide) and base to a mixture of acetonitrile and ivacaftor.methanol solvate to obtain a solution.

In one embodiment, the present invention provides a process for the preparation of crystalline ivacaftor Form G comprising adding a mixture of DMF and diisopropyl ethyl amine to a mixture of acetonitrile and ivacaftor.methanol solvate at an elevated temperature. The reaction mixture is stirred for a period of about 15 minutes to 90 minutes. The reaction mixture is then cooled to about 25-30° C. and crystalline ivacaftor Form G is isolated by methods known in the art such as filtration and centrifugation.

In one embodiment, the present invention provides a process for the preparation of crystalline ivacaftor Form G comprising treating a solution containing ivacaftor.methanol solvate, dimethyl formamide and diisopropyl ethyl amine with a mineral acid such as hydrochloric acid. The crystalline ivacaftor Form G is isolated by methods such as extraction and distillation.

In one embodiment, the present invention provides process for the preparation of crystalline ivacaftor Form G comprising slurrying the crude compound which is isolated by treatment of ivacaftor.methanol solvate with DMF and DIPEA (diiopropyl ethyl amine) in water. The mixture is stirred for a period of about 15 minutes to 90 minutes. The crystalline ivacaftor Form G may be isolated by filtering the above slurry.

In one embodiment, the reaction mixture may be subjected to elevated temperature.

In one embodiment, the present invention provides crystalline ivacaftor Form G by isolating from a suspension of ivacaftor in acetonitrile.

In one embodiment, the present invention provides substantially amorphous ivacaftor Form I.

In one embodiment, the present invention provides substantially amorphous ivacaftor Form I characterized by Differential Scanning calorimetric (DSC) thermogram having an exothermic peak at 222.99±1° C. and an endothermic peak at about 317.98±1° C.

In one embodiment, the present invention provides substantially amorphous ivacaftor Form I characterized by Thermogravimetric Analysis (TGA) thermogram, showing a weight loss of about 0.64% at 100° C. and 0.911% at 185° C. determined over the temperature range of 0° C. to 400° C. and heating rate of 10° C./min.

In one embodiment, the present invention provides substantially amorphous ivacaftor Form I having PXRD pattern which is substantially in accordance with FIG. 13; Differential Scanning calorimetric (DSC) thermogram having an exothermic peak at 222.99±1° C. and an endothermic peak at about 317.98±1° C., which is substantially in accordance with FIG. 14 and Thermogravimetric Analysis (TGA) thermogram, showing a weight loss of about 0.64% at 100° C. and 0.911% at 185° C. determined over the temperature range of 0° C. to 400° C. and heating rate 10° C./min, which is substantially in accordance with FIG. 15.

In one embodiment, the present invention provides substantially amorphous ivacaftor Form I having water content of about 4.33% as measured by Karl Fischer.

In one embodiment, the present invention provides a process for the preparation of substantially amorphous ivacaftor Form I comprising isolating substantially amorphous ivacaftor form I from a 30% aqueous n-butanol solution.

In one embodiment, the present invention provides a process for the preparation of substantially amorphous ivacaftor Form I comprising mixing ivacaftor.methanol solvate and 30% aqueous butanol. The reaction mixture containing ivacaftor.methanol solvate and 30% aqueous n-butanol is heated to a temperature of about 70-90° C. to obtain a clear solution. Preferably, the reaction mixture is heated to a temperature of about 80-85° C. The reaction mixture is cooled to a temperature of about 25-30° C. and isolated by methods known in the art such as filtration and centrifugation.

In one embodiment, the present invention provides substantially amorphous ivacaftor Form II.

In one embodiment, the present invention provides substantially amorphous ivacaftor Form II characterized by Differential Scanning calorimetric (DSC) thermogram having an exothermic peak at 223.13±1° C. and endothermic peak at about 191.5 and 315.6±1° C.

In one embodiment, the present invention provides substantially amorphous ivacaftor form II characterized by Thermogravimetric Analysis (TGA) thermogram, showing a weight loss of about 0.25% at 100° C. and 0.25% at 185° C. determined over the temperature range of 0° C. to 400° C. and heating rate 10° C./min.

In one embodiment, the present invention provides substantially amorphous ivacaftor form II having PXRD pattern which is substantially in accordance with FIG. 16; Differential Scanning calorimetric (DSC) thermogram having an exothermic peak at 223.13±1° C. and endothermic peak at about 191.5 and 315.6±1° C., which is substantially in accordance with FIG. 17 and Thermogravimetric Analysis (TGA) thermogram, showing a weight loss of about 0.25% at 100° C. and 0.25% at 185° C. determined over the temperature range of 0° C. to 400° C. and heating rate 10° C./min, which is substantially in accordance with FIG. 18.

In one embodiment, the present invention provides substantially amorphous ivacaftor Form II having water content of about 1.64% as measured by Karl Fischer.

In one embodiment, the present invention provides a process for the preparation of substantially amorphous ivacaftor Form II comprising isolating substantially amorphous form II from a 10% aqueous n-butanol solution.

In one embodiment, the present invention provides a process for the preparation of substantially amorphous ivacaftor Form II comprising dissolving ivacaftor.methanol solvate in 10% aqueous butanol. The reaction mixture containing ivacaftor.methanol solvate and 10% aqueous n-butanol is heated to a temperature of about 70-90° C. to obtain a clear solution. Preferably, the reaction mixture is heated to a temperature of about 80-85° C. The substantially amorphous ivacaftor form II is obtained by cooling the reaction mixture and isolating by known techniques such as filtration and centrifugation.

In one embodiment, the present invention provides crystalline ivacaftor.propylene glycol solvate.

In one embodiment, the present invention provides crystalline ivacaftor.propylene glycol solvate characterized by X-ray diffraction (XRD) spectrum having peak reflections at about 4.17, 8.38, 12.61, 16.57 and 16.84±0.2 degrees 2 theta and Differential Scanning calorimetric (DSC) thermogram having endothermic peak at about 321.34, 197.03, 187.2, 141.4 and 58.1±1° C.

In one embodiment the present invention provides crystalline ivacaftor.propylene glycol solvate characterized by X-ray diffraction (XRD) spectrum having peak reflections at about 4.17, 8.38, 12.61, 16.57 and 16.84±0.2 degrees 2 theta which is substantially in accordance with FIG. 19.

In one embodiment, the present invention provides crystalline ivacaftor.propylene glycol solvate characterized by Thermogravimetric Analysis (TGA) thermogram, showing a weight loss of about 38:5 at 185° C. determined over the temperature range of 0° C. to 400° C. and heating rate of 10° C./min.

In one embodiment, the present invention provides a process for the preparation of crystalline ivacaftor.propylene glycol solvate comprising isolating ivacaftor.propylene glycol solvate from a propylene glycol solution.

In one embodiment, the present invention provides a process for the preparation of ivacaftor.propylene glycol comprising slurrying ivacaftor in propylene glycol and cooling the propylene glycol solution containing ivacaftor to obtain ivacaftor.propylene glycol solvate.

In one embodiment, ivacaftor is dissolved in propylene glycol at elevated temperature.

In one embodiment, the present invention provides crystalline ivacaftor.DMF solvate.

In one embodiment, the present invention provides crystalline ivacaftor. DMF solvate characterized by X-ray diffraction (XRD) spectrum having peak reflections at about 7.12, 7.55, 17.87, 18.19, and 20.95±0.2 degrees 2 theta.

In one embodiment, the present invention provides crystalline ivacaftor.DMF solvate characterised by Differential Scanning calorimetric (DSC) thermogram having endothermic peak at about 339.67, 272.3, 169.4 and 122.3±1° C.

In one embodiment the present invention provides crystalline ivacaftor.DMF solvate characterized by X-ray diffraction (XRD) spectrum having peak reflections at about 7.12, 7.5, 17.8, 18.1, and 20.9±0.2 degrees 2 theta which is substantially in accordance with FIG. 20.

In one embodiment, the present invention provides crystalline ivacaftor.DMF solvate characterized by Thermogravimetric Analysis (TGA) thermogram, showing a weight loss of about 11.07% at 185° C. determined over the temperature range of 0° C. to 400° C. and heating rate of 10° C./min.

In one embodiment, the present invention provides a process for the preparation of ivacaftor.DMF solvate comprising adding DMF, ethylacetate and a base to ivacaftor to obtain a clear solution. The clear solution is concentrated under vacuum and a mixture of acetonitrile and water is added. The reaction mass is heated and cooled to obtain crystalline ivacaftor. DMF solvate.

In one embodiment, the base used is selected from pyridine, diisopropyl ethyl amine, ammonia. Preferably, the base is diisopropyl ethyl amine.

In one embodiment, the present invention provides crystalline ivacaftor.DMF solvate having a ratio of ivacaftor: DMF of 1:0.4.

In one embodiment, the present invention provides crystalline ivacaftor.THF (tetrahydrofuran) solvate.

In one embodiment the present invention provides crystalline ivacaftor.THF solvate characterized by X-ray diffraction (XRD) spectrum having peak reflections at about 6.28, 12.4, 13.2, 14.8 and 22.6±0.2 degrees 2 theta.

In one embodiment, the present invention provides crystalline ivacaftor.THF solvate characterized Differential Scanning calorimetric (DSC) thermogram having endothermic peak at about 315 and 313±1° C. exothermic peak at about 244±1° C.

In one embodiment the present invention provides crystalline ivacaftor.THF solvate characterized by X-ray diffraction (XRD) spectrum having peak reflections at about 6.28, 12.46, 13.29, 14.83 and 22.63±0.2 degrees 2 theta, which is substantially in accordance with FIG. 21.

In one embodiment, the present invention provides crystalline ivacaftor.THF solvate characterized by Thermogravimetric Analysis (TGA) thermogram, showing a weight loss of about 12.6% at 185° C. determined over the temperature range of 0° C. to 400° C. and heating rate of 10° C./min.

In one embodiment, the present invention provides a process for the preparation of crystalline ivacaftor. THF solvate comprising isolating ivacaftor from a THF solution.

In one embodiment, the present invention provides a process for the preparation of crystalline ivacaftor. THF solvate comprising dissolving ivacaftor in THF and cooling the THF solution containing ivacaftor to obtain crystalline ivacaftor.THF solvate.

In one embodiment, ivacaftor is dissolved in THF at elevated temperature.

In one embodiment, the present invention provides crystalline ivacaftor. THF solvate having a ratio of ivacaftor: THF of 1:0.37.

In one embodiment, the present invention provides crystalline ivacaftor.ethylacetate.DMF solvate.

In one embodiment, the present invention provides crystalline ivacaftor.ethylacetate.DMF solvate characterized by X-ray diffraction (XRD) spectrum having peak reflections at about 4.81, 7.13, 9.67, 14.56 and 17.45±0.2 degrees 2 theta and Differential Scanning calorimetric (DSC) thermogram having endothermic peak at about 287.8±1° C.

In one embodiment the present invention provides crystalline ivacaftor.ethylacetate.DMF solvate characterized by X-ray diffraction (XRD) spectrum having peak reflections at about 4.81, 7.13, 9.67, 14.56 and 17.45±0.2 degrees 2 theta which is substantially in accordance with FIG. 22

In one embodiment, the present invention provides crystalline ivacaftor.ethylacetate.DMF solvate characterized by Thermogravimetric Analysis (TGA) thermogram, showing a weight loss of about 16.9 up to 183° C. % determined over the temperature range of 0° C. to 400° C. and heating rate of 10° C./min.

In one embodiment, the present invention provides a process for the preparation of crystalline ivacaftor.ethylacetate.DMF solvate comprising isolating from a solution of ethylacetate and DMF.

In one embodiment, the present invention provides a process for the preparation of crystalline ivacaftor.ethylacetate.DMF solvate comprising adding DMF to a hot mixture of ivacaftor and ethyl acetate to obtain a clear solution. The clear solution is subjected to cooling to obtain crystalline ivacaftor.ethylacetate.THF solvate.

In one embodiment, the present invention provides crystalline ivacaftor.ethylacetate.DMF solvate having a ratio ivacaftor:ethylacetate:THF of 1:0.22:0.59.

In one embodiment, the present invention provides crystalline ivacaftor Form D characterized by X-ray Diffraction (XRD) spectrum as depicted in FIG. 28.

In one embodiment, the present invention provides crystalline ivacaftor Form D characterized by Differential Scanning calorimetric (DSC) thermogram, which is substantially in accordance with FIG. 29.

In one embodiment, the present invention provides crystalline ivacaftor Form D characterized by X-ray Diffraction (XRD) spectrum having peak reflections at about 4.18 and 4.55±0.2 degrees 2 theta and Differential Scanning calorimetric (DSC) thermogram having an endotherm peak at about 138±1° C. and 318±1° C. and exotherm peak at about 237° C.

In one embodiment, the present invention provides crystalline ivacaftor Form D characterized by X-ray Diffraction (XRD) spectrum, which is substantially in accordance with FIG. 28 and Differential Scanning calorimetric (DSC) thermogram having an endotherm peak at about 138±1° C. and at about 318±1° C. and exotherm peak at about 237±1° C. which is substantially in accordance with FIG. 29.

In one embodiment, the present invention provides crystalline ivacaftor Form D further characterized by Thermogravimetric Analysis (TGA) thermogram, showing a weight loss of about 5.11% determined over the temperature range of 30° C. to 250° C. and heating rate 10° C./min, which is substantially in accordance with FIG. 30.

In one embodiment, the present invention provides crystalline ivacaftor Form E characterized by X-ray Diffraction (XRD) spectrum as depicted in FIG. 31.

In one embodiment, the present invention provides crystalline ivacaftor Form E characterized by Differential Scanning calorimetric (DSC) thermogram, which is substantially in accordance with FIG. 32.

In one embodiment, the present invention provides crystalline ivacaftor Form E characterized by X-ray Diffraction (XRD) spectrum having peak reflections at about 4.26, and 4.60±0.2 degrees 2 theta and Differential Scanning calorimetric (DSC) thermogram having an endotherm peak at about 144° C.±1° C. and 304° C.±1° C. and exotherm peak at about 248±1° C.

In one embodiment, the present invention provides crystalline ivacaftor Form E characterized by X-ray Diffraction (XRD) spectrum having peak reflections at about 4.26, 4.60, 11.92, 20.38±0.2 degrees 2 theta and Differential Scanning calorimetric (DSC) thermogram having an endotherm peak at about 144° C.±1° C. and 304° C.±1° C. and exotherm peak at about 248±1° C.

In one embodiment, the present invention provides crystalline ivacaftor Form E characterized by X-ray Diffraction (XRD) spectrum, which is substantially in accordance with FIG. 31 and Differential Scanning calorimetric (DSC) thermogram having an endotherm peak at about 144° C.±1° C. and 304±1° C. and exotherm peak at about 248±1° C. which is substantially in accordance with FIG. 32.

In one embodiment, the present invention provides crystalline ivacaftor Form E further characterized by Thermogravimetric Analysis (TGA) thermogram, showing a weight loss of about 3.63% determined over the temperature range of 30° C. to 250° C. and heating rate 10° C./min, which is substantially in accordance with FIG. 33.

In one embodiment, the present invention provides crystalline ivacaftor Form E1 characterized by X-ray Diffraction (XRD) spectrum, which is substantially in accordance with FIG. 34.

In one embodiment, the present invention provides crystalline ivacaftor Form E1 characterized by Differential Scanning calorimetric (DSC) thermogram, which is substantially in accordance with FIG. 35.

In one embodiment, the present invention provides crystalline ivacaftor Form E1 characterized by X-ray Diffraction (XRD) spectrum having peak reflections at about 4.48 and 8.87±0.2 degrees 2 theta and Differential Scanning calorimetric (DSC) thermogram having an endotherm at about 142° C.±1° C. and 306° C.±1° C. and exotherm at about 250±1° C.

In one embodiment, the present invention provides crystalline ivacaftor Form E1 characterized by X-ray Diffraction (XRD) spectrum, which is substantially in accordance with FIG. 34 and Differential Scanning calorimetric (DSC) thermogram having an endotherm peak at about 144° C.±1° C. and 304° C.±1° C. and exotherm peak at about 248±1° C. which is substantially in accordance with FIG. 35.

In one embodiment, the present invention provides crystalline ivacaftor Form E1 further characterized by Thermogravimetric Analysis (TGA) thermogram, showing a weight loss of about 3.34% determined over the temperature range of 30° C. to 250° C. and heating rate 10° C./min, which is substantially in accordance with FIG. 36.

In one embodiment, the present invention provides a process for the preparation of ivacaftor, a compound of formula I,

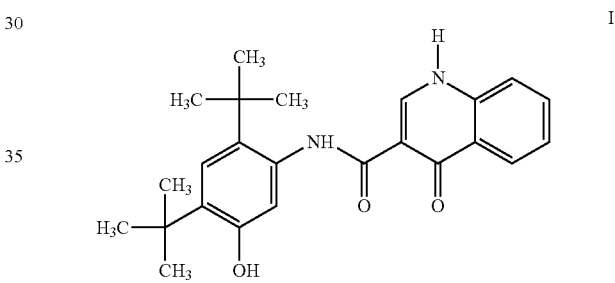

comprising cyclising a compound of formula IV

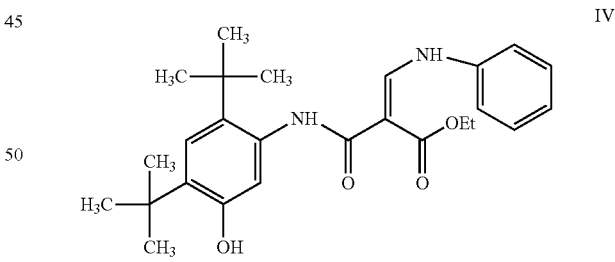

In one embodiment, the above process may be carried out in the presence or absence of a suitable solvent and a suitable cyclising agent selected from the group consisting of phosphoric acid in the presence of phosphoryl chloride, eaton's reagent, trifluoroacetic anhydride-acetic acid and phosphorus pentoxide and the like.

Suitable solvent may be selected from the group consisting of nitriles such as acetonitrile, butyronitrile, propionitrile and the like; hydrocarbon such as n-hexane, cyclohexane, toluene, xylene and the like; halogenated solvents such as, methylene dichloride, ethylene dichloride, chloroform, carbon tetrachloride or a mixture thereof.

In one embodiment, the present invention provides a process for the preparation of a compound of formula IV comprising reacting a compound of formula II with a compound of formula III.

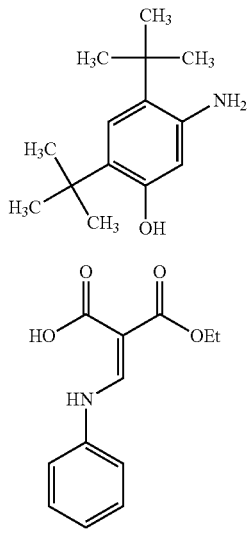

In one embodiment, the above process may be carried out in the presence of a coupling agent selected from HATU, (O-(7-azabenzotriazol-1-yl)-N,N,N',N'-tetramethyluronium hexafluorophosphate), BOP (Benzotriazol-1-yloxy)tris(dimethylamino)phosphonium hexafluorophosphate), HBTU O-Benzotriazole-N,N,N,N-tetramethyl-uronium-hexafluoro-phosphate and PFP-TFA pentafluorophenyltrifluoroacetate, DIC (N,N-Diisopropylcarbodiimide), EDC 1-Ethyl-3-(3-dimethyllaminopropyl)carbodiimide, TBTU O-(Benzotriazol-1-yl)-N,N,N,N'-tetramethyluronium tetrafluoroborate, DCC (N,N'-dicyclohexylcarbodiimide), PyBOP® (benzotriazol-1-yl-oxytripyrrolidinophosphonium hexafluorophosphate, Isobutyl chloroformate and 1-methyl-2-chloropyridinium iodide.

In one embodiment, the above reaction may be carried out in presence of a suitable solvent selected from the group consisting of nitriles such as acetonitrile, butyronitrile, propionitrile and the like; hydrocarbon such as n-hexane, cyclohexane, toluene, xylene and the like; halogenated solvents such as, methylene dichloride, ethylene dichloride, chloroform, carbon tetrachloride and the like; amides such as dimethylformamidedimethylacetamide and the like; ethers such as tetrahydrofuran, diethyl ether, diisopropyl ether and the like.

In one embodiment, the present invention provides a compound of formula IV

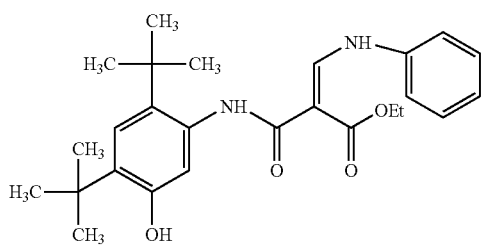

In one embodiment, the present invention provides a process for preparing a compound of formula I, comprising:

a) methanolysis of a compound of formula V to obtain a compound of formula III; and

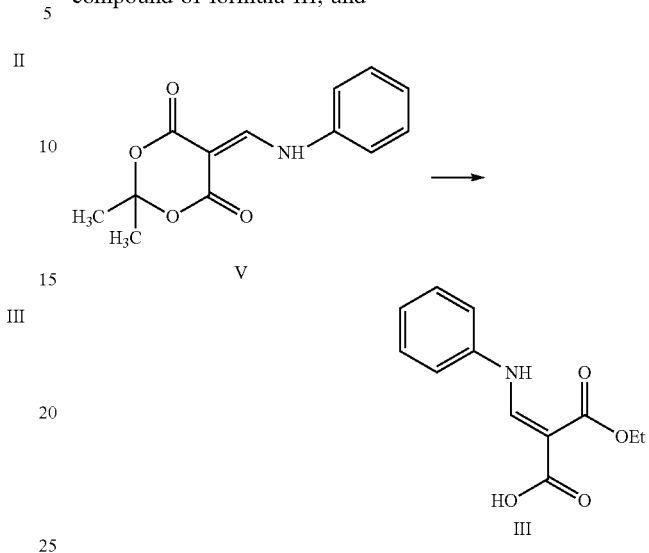

b) converting the compound of formula III to a compound of formula I.

In one embodiment, step a) of the above process is carried out in the presence of a suitable solvent and a suitable base.

Suitable solvents may be selected from water, alcohols such as methanol, ethanol, n-propanol, isopropanol or a mixture thereof.

A suitable base may be selected from an organic or an inorganic base. The inorganic base may be selected from the group consisting of hydroxides such as sodium hydroxide, potassium hydroxide, calcium hydroxide; alkoxides such as sodium methoxide, potassium methoxide, sodium tert-butoxide, potassium tert-butoxide; carbonates such as sodium carbonate, potassium carbonate; bicarbonates such as sodium bicarbonate, potassium bicarbonate and the like; organic base may be selected from triethyl amine, trimethyl amine, diisopropyl ethylamine, dimethyl amino pyridine, picoline, dimethyl amino pyridine and pyridine.

In one embodiment, in step b) of the above process compound of formula III is converted to a compound of formula I by process described herein above, In one embodiment, the present invention provides the use of compound of formula III or V in the preparation of a compound of formula I.

In one embodiment, the present invention provides a process for the preparation of compound of formula I as represented schematically in scheme 1, wherein the process neither includes chromatographic separation nor chromatographic purification.

Scheme 1:

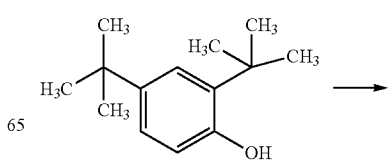

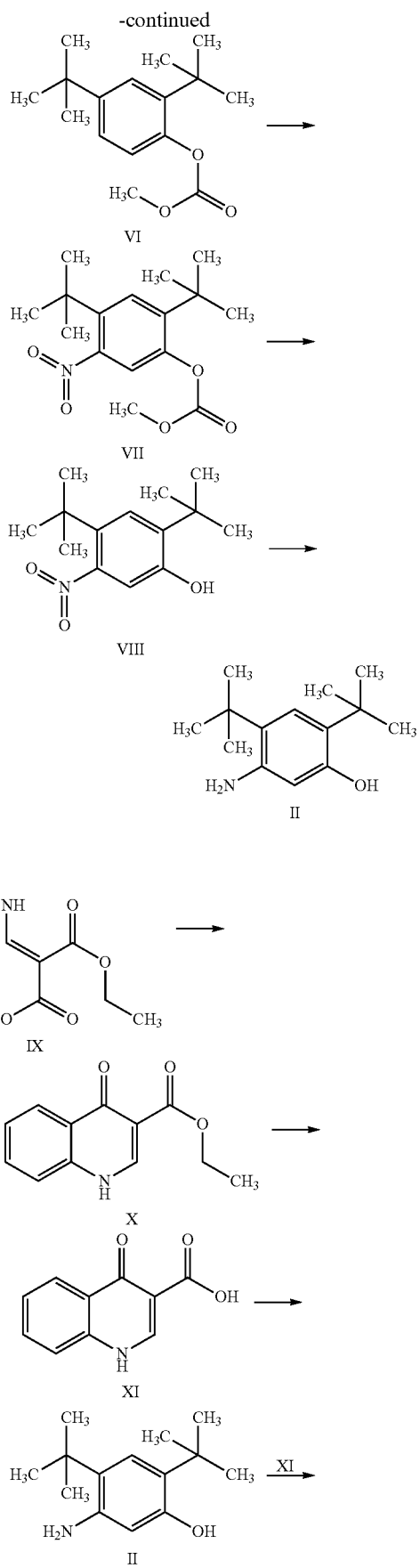

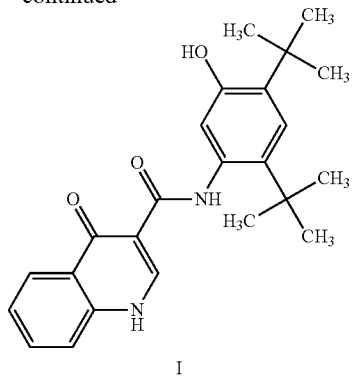

In one embodiment, in the above scheme, 2,4-di-ter-butyl-5-nitro-phenyl methyl carbonate, a compound of formula VII, which is free of 2,4-di-ter-butyl-6-nitro-phenyl methyl carbonate is prepared by reacting a compound of formula VI with concentrated nitric acid and sulfuric acid to obtain compound of formula VII followed by purification in a suitable solvent.

Suitable solvent may be selected from the group consisting of hydrocarbons such as hexane, toluene, cyclohexane and xylene; ethers like diethyl ether, diisopropyl ether, methyl tert-butyl ether, tetrahydrofuran; ketones like acetone, methyl ethyl ketone, and a mixture thereof. Preferably, the solvent is hexane or methanol. Preferably the solvent is methanol.

In one embodiment, the compound of formula VII is treated with methanol to obtain a solution. The solution of compound of formula VII in methanol may be achieved by heating the mixture of compound of formula VII in methanol at a temperature of about 45 to about 55° C. The solution is then cooled to a temperature of about 25 to about 30° C.

In one embodiment, in the above scheme, compound of formula VII is hydrolysed to obtain compound of formula VIII.

Hydrolysis may be carried out using suitable base selected from the group consisting of hydroxides such as sodium hydroxide, potassium hydroxide; alkoxides such as sodium methoxide, tert-butoxide or a suitable acid such as hydrochloric acid, sulphuric acid and the like. Preferably, hydrolysis is carried out using is potassium hydroxide.

In one embodiment, the compound of formula VII is reacted with potassium hydroxide in methanol at a temperature of about 25 to about 30° C. to obtain a compound of formula VIII.

The compound of formula VIII is optionally purified using suitable solvent like alcohols, water or a mixture thereof.

Suitable solvent may be selected from the group consisting of hydrocarbons such as hexane, toluene, cyclohexane and xylene; ethers like diethyl ether, diisopropyl ether, methyl tert-butyl ether, tetrahydrofuran; ketones like acetone, methyl ethyl ketone, or a mixture thereof. Preferably the solvent is hexane.

In one embodiment, in the above scheme, the compound of formula VIII is treated with a suitable reducing agent to obtain a compound of formula II.

Suitable reducing agent may be selected from the group consisting of palladium, palladium/C, palladium hydroxide, Raney nickel, ammonium formate, tin-chloride.

In one embodiment, the compound of formula VIII is converted to compound of formula II using catalyst is palladium on carbon. The palladium content in the catalyst may be about 5% to about 20% wt/wt % on carbon, preferably about 10% wt/wt % on carbon. The pressure for hydrogenation can range from about 0.5 kg/cm² g to about 20 kg/cm² g by using hydrogen gas, preferably about 4·kg/cm² g to about 8 kg/cm² g, more preferably about 5·kg/cm² g to about 6 kg/cm² g.

The reaction may be carried out at a temperature of about 25° C. to about reflux temperature of the solvent. The reaction is carried out over a period of about 30 minutes to about 3 hours. Preferably, the reaction is carried out in methanol at a temperature of about 25° C. to about 30° C. over a period of about 30 min to about 1 hour to obtain a compound of formula II.

The compound of formula II is purified in a suitable solvent.

Suitable solvent may be selected from the group consisting of hydrocarbons such as hexane, toluene, cyclohexane and xylene; ethers such as diethyl ether, diisopropyl ether, methyl tert-butyl ether, tetrahydrofuran; ketones such as acetone, methyl' ethyl ketone or a mixture thereof. Preferably the solvent is hexane.

In one embodiment, the compound of formula II is mixed with hexane to obtain a slurry.

The slurry is stirred and maintained for a period of about 30 min to about 1 hour. Preferably, the slurry is stirred and maintained for a period of about 1 hour and filtered.

In one embodiment, the present invention provides a process for the preparation of the compound of formula I, comprising:

a) converting compound of formula IX to a compound of formula X

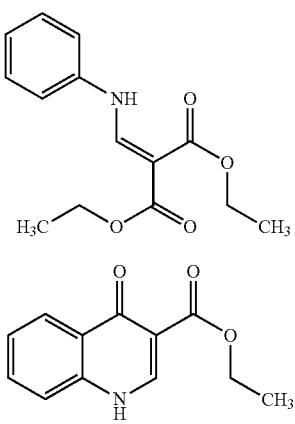

IX in the presence of Eaton's reagent;
b) hydrolysis of compound of formula X to obtain the compound of formula XI;

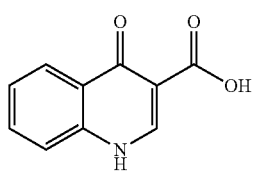

XI

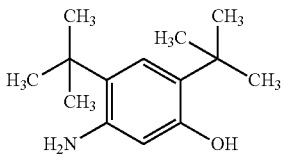

II c) reacting the compound of formula XI with a compound of formula II to obtain ivacaftor, the compound of formula I.

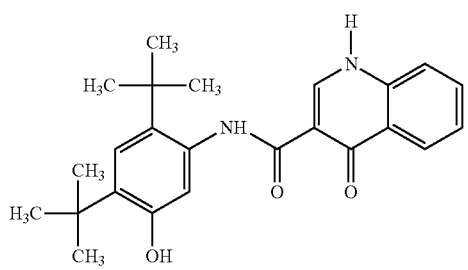

I

In one embodiment, in step a) of the above process, the compound of formula IX is converted to a compound of formula X in the presence of Eaton's reagent.

In one embodiment, eatons reagent is prepared by mixing phosphorous pentoxide and methane sulfuric acid.

In one embodiment, phosphorous pentoxide and methane sulfonic acid are mixed at a temperature of about 25 to about 30° C. under nitrogen atmosphere.

In one embodiment, the compound of formula IX is converted to compound of formula X in the presence or absence of a solvent. Preferably, reaction is carried out in absence of a solvent.

The reaction transpires over a temperature range of about 0-150° C. Preferably, the reaction transpires at a temperature of about 80-85° C.

In one embodiment, the compound of formula X is purified using suitable solvents selected from the group consisting of water, hydrocarbon such as hexane, toluene and the like; alcohols such as methanol, ethanol and the like, ketones such as acetone, methyl ethyl ketone and the like; ethers such as diethyl ether, diisopropyl ether and the like or mixtures thereof.

Preferably, the solvent is a mixture of water and acetone.

In one embodiment, the compound of formula X is heated in a mixture of acetone and water to a temperature of about 45 to about 50° C. The mixture is then cooled to a temperature of about 25 to about 30° C. and isolated by methods known in the art such as filtration, centrifugation and the like.

In one embodiment, in step b) of the above process compound of formula X is converted to a compound of formula XI by hydrolysis.

In one embodiment, the hydrolysis may be carried out using a suitable base selected from the group consisting of hydroxides such as sodium hydroxide, potassium hydroxide; alkoxides such as sodium methoxide, tert-butoxide or a suitable acid such as hydrochloric acid, sulphuric acid and the like. Preferably, hydrolysis is carried using sodium hydroxide.

In embodiment, the compound of formula X is hydrolysed to a compound of formula XI using aqueous sodium hydroxide.

The hydrolysis transpires at a temperature of about 25 to about reflux temperature of the solvent. Preferably, the reaction transpires at a temperature of about 80 to about 85° C.

The compound of formula XI thus obtained is purified in a suitable solvent selected from the group consisting of ethers such as diethyl ether, diisopropyl ether and the like; esters such as ethyl acetate, isopropyl acetate and the like; alcohols such as ethanol methanol, isopropanol, and the like. Preferably, the solvent is methanol.

In one embodiment, the compound of formula XI is treated with methanol to obtain a slurry. The slurry is stirred and maintained for a period of about 30 min to about 90 min. Preferably, the slurry is maintained for a period of about 60 min and isolated by known methods in the art such as filtration, centrifugation and the like. Preferably, the compound of formula XI is isolated by filtration.

In one embodiment, in step c) of the above process, the compound of formula XI is reacted with a compound of formula II to obtain ivacaftor, the compound of formula I.

In one embodiment, the process comprises reacting compound of formula II and the compound of formula XI in the presence of a coupling agent selected from HATU (O-(7-azabenzotriazol-1-yl)-N,N,N',N'-tetramethyluronium-hexafluorophosphate), BOP (Benzotriazol-1-yloxy)tris (dimethylamino)phosphonium hexafluorophosphate), HBTU O-Benzotriazole-N,N,N,N'-tetramethyl-uronium-hexafluoro-phosphate and PFP-TFA pentafluorophenyltrifluoroacetate. Preferably, the reaction is carried out in presence of HATU.

In one embodiment, the reaction may be carried out in presence of suitable solvent and a suitable base.

A suitable base may be organic or inorganic bases. Inorganic base may be selected from the group consisting of hydroxides such as sodium hydroxide, potassium hydroxide, calcium hydroxide, lithium hydroxide; alkoxides such as sodium methoxide, potassium methoxide, sodium tert-butoxide, potassium tert-butoxide; carbonates such as sodium carbonate, potassium carbonate, bicarbonates such as sodium bicarbonate, potassium bicarbonate and the like. Organic bases may be selected from the group consisting of triethyl amine, trimethyl amine, pyridine, diisopropyl ethyl amine, pyridine and dimethyl amino pyridine. Preferably, the base is diisopropyl ethyl amine.

A suitable solvent may be selected from, but is not limited to halogenated hydrocarbons such as methylene chloride, ethylene chloride, chloroform and carbon tetrachloride; alcohols such as methanol, ethanol, 1-propyl alcohol, 2-propanol, tert-butanol; esters such as ethyl acetate, isopropyl acetate and butyl acetate; amides such as formamide, N,N-dimethylformamide, N,N-dimethylacetamide; dimethyl sulfoxide; nitrile such as acetonitrile, propionitrile; ethers such as diethyl ether, diisopropyl ether, t-butyl methyl ether, 1,4-dioxane, tetrahydrofuran; hydrocarbons such as benzene, toluene, cyclohexane, methyl cyclohexane and toluene; or mixtures thereof. Preferably, the solvent is N,N-dimethylformamide.

In one embodiment, the compound of formula XI is reacted with a compound of formula II in the presence of diisopropyl ethyl amine and HATU in N, N dimethyl formamide.

The reaction transpires over a period of about 4 to about 10 hours at a temperature of about 35 to about 55° C. Preferably, the reaction transpires over a period of about 6 to about 7 hours at a temperature for about 40 to about 45° C.

In one embodiment, the present invention provides a process for preparation of compound of formula I, comprising isolating compound of formula I from the reaction mixture from a suitable solvents selected from water, nitriles, esters, alcohols, hydrocarbons, halogenated hydrocarbons, acetates, amides, sulfoxides, ethers. Preferably, ivacaftor is isolated from a mixture of nitrile such as acetonitrile and water. More preferably, ivacaftor, the compound of formula I isolated from ethyl acetate.

Instrumental Settings for XRPD:

The measurements were performed on Philips X-Ray Diffractometer model XPERT-PRO (PANalytical) Detector: X'celerator [1] using Cu lamp with type and wavelength of the X-ray radiation: K-$\alpha_1$ 1.54060 [Å], K-$\alpha_2$ 1.5444 [Å] under the following conditions: The measurements were carried out with a Pre FIX module programmable divergence slit and anti-scatter Slit (Offset 0.00°); Generator settings: 40 mA/45 kV, tube current 40 mAmp Time per step: 50 s, Step size: 0.0167, Peak width 2.00 and start angle)(° 2.0 and End angle: 50.0; Scan type: continuous; measurement performed at 25° C. The XRPD instrument is calibrated using NIST SRM 6-40C silicon standard and NIST SRM 1976 Alumina.

Sample preparation: Take an adequate amount of the sample to fill the sample holder using back-loading technique. Then load the sample holder between the X-ray optics-path and scan using the above described parameters. Integrate the obtained powder X-ray diffraction profiles using X'Pert HighScore Plus Software.

Instrumental Settings for DSC:

The DSC thermogram was measured by a Differential Scanning calorimeter (DSC 822, Mettler Toledo) at a scan rate of 10° C. per minute in the temperature range of range is "25° C. to 350° C.". The DSC module was calibrated with Indium and zinc standard.

Method:

An empty aluminum standard 40 µl was taken and put on the microbalance. Tared and weighed approximately about 2.0-3.0 mg of sample. The cover or lid of the pan was slightly pierced and sealed. The sample pan was placed in the left position of mark 'S' and empty pan was placed in the right position on mark 'R' of the DSC sensor. The furnace lid was placed. The method was selected.

Instrumental Settings for TGA:

Instrument Name: TGA Q 500; Method: 5-8 mg of sample was taken in platinum pan and heated at 10° C./minute from 0 to 400° C.

Instrumental Settings for Infrared Spectrophotometry:

Instrument Name: Perkin Elmer; Model: Spectrum 1; Method: 300-400 mg of KBr, previously dried at 200° C. and cooled was taken into a mortar and ground to a fine powder. 1.0 mg-2.0 mg of test sample, was added and mixed well and ground to a fine powder. A small quantity of powder was taken and a thin semitransparent pellet was made. The IR spectrum of the pellet was recorded from 4000 cm$^{-1}$ to 650 cm$^{-1}$ taking air as a reference.

Instrumental Settings for GC (Gas Chromatography) Chromatographic Parameters:

Instrument: Gas chromatograph equipped with FID detector and Headspace; Column: DB-1, 60 m×0.32 mm, 5.0 µm, Column Temp.: 40° C. to 240° C. @ 20° C./minute; Injector/detector: 200° C./270° C., Carrier gas: Nitrogen; Linear velocity: 20 cm/sec, Pressure Ramp: 10.9 psi to 18 psi @ 7 psi/minute, Split Ratio: (5:1), Diluent: Benzyl alcohol (HPLC and GC grade)

The following examples are provided to enable one skilled in the art to practice the invention and are merely illustrative of the invention. The examples should not be read as limiting the scope of the invention

EXAMPLES

Example 1

Crystalline Ivacaftor Form G'

Ivacaftor (4 gms) and n-butanol (60 ml) was heated to 80-85° C. to obtain a clear solution. The solution was stirred at 80-85° C. for 1 hr. The solution was cooled to 30-35° C. and stirred for 1 hr. The solid was filtered and dried at 65-70° C. for 12 hrs. Dried material was jet milled and dried further at 65-70° C. for about 90 hours to get 1.92 gm. (DSC) endothermic peak at about 186.77 and 318.08±1° C. and exothermic peak at about 221.87±1° C., Water content: 2.29%, Butanol content: 4424 ppm.

XRD Table of Form G'

| Pos. [°2Th.] | d-spacing [Å] | Rel. Int. [%] |
| --- | --- | --- |
| 4.984 | 17.73 | 24.97 |
| 7.24 | 12.19 | 44.29 |
| 7.62 | 11.59 | 47.33 |
| 10 | 8.84 | 26.27 |
| 10.57 | 8.36 | 28.05 |
| 11.51 | 7.68 | 12.96 |
| 12.83 | 6.89 | 40.99 |
| 13.27 | 6.66 | 19.97 |
| 14.31 | 6.18 | 100 |
| 15.63 | 5.66 | 33.26 |
| 16.64 | 5.32 | 16.6 |
| 18.072 | 4.9 | 23.22 |
| 19.08 | 4.64 | 46.8 |
| 20.02 | 4.43 | 67.21 |
| 20.68 | 4.29 | 32.12 |
| 21.76 | 4.08 | 41.7 |
| 22.99 | 3.86 | 15.15 |
| 23.62 | 3.76 | 19.39 |
| 25.59 | 3.48 | 13.73 |
| 26.91 | 3.31 | 5.33 |
| 27.77 | 3.21 | 9.86 |
| 28.4 | 3.14 | 10.91 |
| 28.76 | 3.1 | 15.83 |
| 29.84 | 2.99 | 10.56 |
| 35.67 | 2.51 | 4.79 |
| 36.86 | 2.43 | 3.92 |
| 43.71 | 2.07 | 2.57 |

Example 2

Crystalline Ivacaftor n-Butanol Solvate

Ivacaftor (4 gms) and n-butanol (60 ml) was heated to 80-85° C. to obtain a clear solution. The solution was stirred at 80-85° C. for 1 hr. The solution was cooled to 30-35° C. and stirred for 1 hr. The solid was filtered and dried at 50-55° C. for 2 hrs to obtain 3.2 gm. DSC endothermic peak at about 315.25, 184.91, 156.06, 150.74 and 103.25±1° C. and exothermic peak at 231.68±1° C., Butanol content by G.C (gas chromatography): 137926 ppm.

XRD of Butanol Solvate

| Pos. [°2Th.] | d-spacing [Å] | Rel. Int. [%] |
| --- | --- | --- |
| 2.5 | 35.21 | 0.46 |
| 4.98 | 17.71 | 69.01 |
| 5.91 | 14.94 | 100 |
| 6.37 | 13.87 | 16.87 |
| 8.1 | 10.9 | 3.11 |
| 8.43 | 10.48 | 1.16 |
| 9.89 | 8.93 | 9.34 |
| 10.53 | 8.39 | 5.23 |
| 11.81 | 7.49 | 13.8 |
| 12.3 | 7.19 | 7.13 |
| 12.75 | 6.93 | 24.07 |
| 13.14 | 6.73 | 9.29 |
| 14 | 6.32 | 6.67 |
| 14.48 | 6.11 | 20.98 |
| 14.83 | 5.97 | 26.81 |
| 16.1 | 5.5 | 3.88 |
| 16.63 | 5.33 | 1.84 |
| 16.93 | 5.23 | 1.25 |
| 17.67 | 5.018 | 2.85 |
| 18.63 | 4.761 | 7.46 |
| 19.14 | 4.63 | 13.39 |
| 19.45 | 4.56 | 21.18 |
| 19.79 | 4.485 | 18.68 |
| 20.19 | 4.39 | 14.69 |
| 21.53 | 4.12 | 20.13 |
| 22.13 | 4.01 | 4.4 |
| 22.59 | 3.93 | 2.52 |
| 23.57 | 3.77 | 17.07 |
| 24.35 | 3.65 | 6.29 |
| 24.74 | 3.59 | 9.7 |
| 25.59 | 3.48 | 5.93 |
| 27.33 | 3.26 | 9.15 |
| 28.01 | 3.18 | 5.39 |
| 28.8 | 3.09 | 10.52 |
| 29.78 | 2.99 | 3.71 |
| 30.75 | 2.9 | 2.36 |
| 32.63 | 2.74 | 0.96 |
| 35.16 | 2.55 | 2.43 |
| 36.55 | 2.45 | 2 |
| 37.52 | 2.39 | 0.56 |
| 39.13 | 2.3 | 1.41 |
| 39.96 | 2.25 | 1.93 |
| 44.18 | 2.05 | 0.74 |
| 46.84 | 1.93 | 0.92 |
| 48.43 | 1.87 | 0.59 |

Example 3

Crystalline Ivacaftor.Methanol Solvate

A mixture of 4-oxo-1,4-dihydroquinoline-3-carboxylic acid (10.0 gm), HATU (24.12 gm), Di-isopropyl ethyl amine (20.56 ml) and DMF (60.0 ml) was stirred for 30 minutes. 5-amino-2-4-di-tert-butyl-phenol (12.8 gm) was added to the reaction mass and stirred for a period of about 15.0 hr. Water was added to the reaction mass and product was extracted with ethyl acetate. Organic layer was washed with 10% sodium carbonate solution followed by brine. Organic layer was distilled under vacuum. 100 ml of methanol was added to obtained residue and heated to 60-65° C. for 30 min. The solid was filtered and dried at 50-55° C. for 12 hrs to obtain 15.1 gm of title compound, (DSC) thermogram having endothermic peak at about 320.88, 192 0.13±1° C. and exothermic peak at 245.63±1° C. water content (by K.F): 0.34%, HPLC purity: 99.86%

XRD Table of Ivacaftor. Methanol Solvate

| Pos. [°2Th.] | d-spacing [Å] | Rel. Int. [%] |
| --- | --- | --- |
| 7.28 | 12.14 | 78.87 |
| 9.31 | 9.49 | 5.2 |
| 9.82 | 9 | 1.59 |
| 10.25 | 8.62 | 19.86 |
| 10.83 | 8.16 | 45.01 |
| 11.18 | 7.91 | 7.2 |
| 13.06 | 6.77 | 64.44 |
| 13.23 | 6.69 | 29.61 |
| 13.84 | 6.39 | 63.67 |
| 14.03 | 6.31 | 100 |
| 14.48 | 6.11 | 2.83 |
| 15.32 | 5.78 | 4.36 |
| 15.85 | 5.59 | 28.4 |
| 16.02 | 5.53 | 9.09 |
| 16.91 | 5.24 | 10.75 |
| 18 | 4.92 | 21.05 |
| 18.78 | 4.72 | 6.96 |
| 19.59 | 4.52 | 26.31 |
| 19.78 | 4.48 | 75.38 |
| 20.27 | 4.37 | 26.9 |
| 20.47 | 4.33 | 63.94 |
| 20.92 | 4.24 | 84.91 |
| 21.76 | 4.08 | 13.83 |
| 22.15 | 4.01 | 6.02 |
| 22.44 | 3.96 | 10.58 |
| 22.98 | 3.86 | 16.54 |
| 23.52 | 3.78 | 24.75 |
| 24.56 | 3.62 | 1.81 |
| 25.38 | 3.506 | 17.11 |
| 25.5 | 3.49 | 28.43 |
| 26.18 | 3.4 | 10.22 |
| 26.4 | 3.37 | 14.66 |
| 26.5 | 3.36 | 13.66 |
| 27.02 | 3.29 | 17.86 |
| 27.54 | 3.23 | 4.85 |
| 28.16 | 3.16 | 47.25 |
| 28.49 | 3.13 | 11.07 |
| 29.09 | 3.06 | 9.97 |
| 29.7 | 3 | 8.59 |
| 30.38 | 2.94 | 3.32 |
| 30.76 | 2.9 | 2.73 |
| 31.55 | 2.83 | 4.25 |
| 32.34 | 2.76 | 4.31 |
| 33.97 | 2.63 | 2.96 |
| 34.49 | 2.6 | 1.77 |
| 35.38 | 2.53 | 2.49 |
| 36.11 | 2.48 | 4.22 |
| 36.73 | 2.44 | 2.9 |
| 37.13 | 2.42 | 1.31 |
| 39.65 | 2.27 | 2.19 |
| 40.34 | 2.23 | 4.43 |
| 41.45 | 2.17 | 1.08 |
| 41.89 | 2.15 | 1.69 |
| 42.81 | 2.11 | 5.17 |
| 43.66 | 2.07 | 3.84 |
| 44.29 | 2.04 | 1.53 |
| 45.02 | 2.01 | 0.72 |
| 45.74 | 1.98 | 0.86 |
| 46.79 | 1.94 | 0.76 |
| 47.62 | 1.9 | 1.48 |
| 48.6 | 1.873 | 1.11 |

Example 4

Crystalline Ivacaftor Form G

10% Aqueous acetonitrile (40 ml) and of ivacaftor methanol solvate (4.0 gm, obtained in ex 3 were charged in a flask. The reaction mixture was heated to 70-75° C. and solution-A (A=DMF+DIPEA=20 ml+8.0 ml) was added gradually to get clear reaction solution. The solution was maintained at this temp for 15 to 20 min. The solution was cooled to 25-30° C. and was stirred for 2.0 hrs. The solid obtained was filtered and washed with acetonitrile and dried under vacuum at 45° C. for 12 hrs to obtain 3.5 gm of title product, (DSC): endothermic peak at about 322.1 and 169.6±1° C. exothermic peak at about 240.4±1° C. water content (by KF): 1.85%, Melting range: 201.8-205.3° C., DIPEA content (diisopropyl ethyl amine: 64000 ppm.

XRD Table of Ivacaftor Form G

| Pos. [°2Th.] | d-spacing [Å] | Rel. Int. [%] |
| --- | --- | --- |
| 5.34 | 16.53 | 100 |
| 5.99 | 14.75 | 9.43 |
| 6.58 | 13.42 | 12.98 |
| 8.38 | 10.54 | 2.21 |
| 9.69 | 9.12 | 21.81 |
| 9.97 | 8.86 | 1.4 |
| 10.72 | 8.24 | 39.2 |
| 11.46 | 7.72 | 12.26 |
| 11.63 | 7.6 | 10.35 |
| 12.09 | 7.31 | 39.59 |
| 12.33 | 7.17 | 4.73 |
| 12.78 | 6.92 | 18.48 |
| 13.24 | 6.68 | 15.65 |
| 14.01 | 6.32 | 19.08 |
| 14.63 | 6.05 | 15.28 |
| 15.21 | 5.82 | 30.87 |
| 15.72 | 5.63 | 1.09 |
| 16.17 | 5.47 | 2.79 |
| 16.7 | 5.3 | 15.55 |
| 16.99 | 5.21 | 51.68 |
| 17.14 | 5.17 | 30.53 |
| 17.5 | 5.06 | 6.04 |
| 18.15 | 4.88 | 84.02 |
| 18.74 | 4.73 | 11.46 |
| 19.3 | 4.59 | 10.57 |
| 19.5 | 4.55 | 11.35 |
| 20.14 | 4.4 | 6.15 |
| 20.7 | 4.28 | 9.42 |
| 20.7 | 4.28 | 9.42 |
| 21.01 | 4.22 | 4.57 |
| 21.6 | 4.11 | 8.44 |
| 21.85 | 4.06 | 9.5 |
| 22.11 | 4.01 | 2.57 |
| 22.55 | 3.94 | 1.38 |
| 23.46 | 3.79 | 19.77 |
| 24.29 | 3.66 | 14.7 |
| 25.69 | 3.46 | 43.01 |
| 26.64 | 3.34 | 16.47 |
| 27.32 | 3.26 | 2.6 |
| 28.17 | 3.16 | 1.63 |
| 29.16 | 3.06 | 8.26 |
| 29.56 | 3.02 | 4.23 |

Example 5

Substantially Amorphous Ivacaftor Form I

Ivacaftor methanol solvate (3.0 g) and 30% aq.n-butanol (45 ml) was heated to 80-85° C. to obtained clear solution. The solution was stirred for 30 min at 80-85° C. and then cooled gradually to 25-30° C. and stirred for 60 min. at 25-30° C. The product was filtered, washed with n-Butanol. Product was dried in air drier at 65-70° C. to obtain 2.5 gm of title compound. DSC exothermic peak: 222.99±1° C. and an endothermic peak: 317.98±1° C.; water content (by K.F): 4.33%

XRD Table of Amorphous Form I

| Pos. [°2Th.] | d-spacing [Å] | Rel. Int. [%] |
|---|---|---|
| 5.41 | 16.32 | 100.00 |
| 7.47 | 11.81 | 21.44 |
| 14.12 | 6.27 | 22.64 |
| 18.92 | 4.68 | 38.25 |
| 21.58 | 4.11 | 26.86 |

Example 6

Substantially Amorphous Ivacaftor Form II

Ivacaftor methanol solvate (3.0 g) and 10% aq.n-butanol (30 ml) was heated to 80-85° C. to obtained clear solution. The solution was stirred for 30 min at 80-85° C. and then cooled gradually to 25-30° C. and stirred for 60 min. at 25-30° C. The product was filtered, washed with n-Butanol. Product was dried in air drier at 65-70° C. to obtain 2.5 gm of title compound. DSC exothermic peak: 223.13±1° C. and endothermic peak: 191.5 and 315.6±1° C.; water content (by K.F): 1.64

XRD Table of Amorphous Form II

| Pos. [°2Th.] | d-spacing [Å] | Rel. Int. [%] |
|---|---|---|
| 5.31 | 16.61 | 100.00 |
| 6.92 | 12.75 | 19.49 |

Example 7

Crystalline Ivacaftor Propylene Glycol

Ivacaftor (2 gms) and propylene glycol (30 ml) was heated to 75-80° C. The reaction mixture was maintained for 5 hours at 75-80° C. and then cooled to 25-30° C. and stirred for 1 hr. The solid was filtered and dried at 50-55° C. for 12 hrs to obtain 2.3 gm of title product.

XRD: 4.17, 8.38, 12.61, 16.57 and 16.84±0.2 degrees 2 theta; water content (by K.F): 3.44%, purity (HPLC): 99.98%.

Example 8

Crystalline Ivacaftor DMF Solvate

A mixture of dimethyl formamide (6.25 ml), ethyl acetate (40.62 ml) and diisopropyl ethyl amine (DIPEA 3.12 ml) was added to ivacaftor (5 gms, obtained in example 3) to get clear solution. The solution was concentrated under vacuum and a mixture of acetonitrile and water (20.0 ml; 9:1) was charged. The reaction mixture was heated to about 65-70° C. to get clear solution. The reaction mixture was cooled to 25-30° C. and stirred for 3 hours. The precipitated product was filtered and washed with acetonitrile and dried under vacuum 40-45° C. to get 3.2 gm of title product.

XRD: 7.12, 7.55, 17.87, 18.19, and 20.95±0.2 degrees 2 theta; Melting Range: 201.8-205.3° C., water content (by KF): 1.85, purity by HPLC: 99.38%.

Example-9

Crystalline Ivacaftor THF Solvate

Ivacaftor (10 gms) and THF (90 ml) was heated to get clear a solution. The solution was cooled to 25-30° C. and stirred for 2 hr. Filtered the solid obtained and dried at 50-55° C. for 12 hrs. Weight of dry product=6.5 gm. Purity by HPLC: 99.66%; PXRD: peaks at 6.28, 12.46, 13.29, 14.83 and 22.63±0.2 degrees 2 theta; Water content (by KF): 2.92; Melting Range: 207-209° C., purity: 99.66%

Example 10

Crystalline Ivacaftor.Ethylacetate.DMF Solvate

Ethyl acetate (25 ml) and ivacaftor (5 gms, obtained in example 3) were heated to 70-75° C. dimethyl formamide (7.5 ml) was added to reaction mass to get clear solution and the solution was maintained at this temp for 15-20 mins. The reaction mass was cooled to 25-30° C. and stirred for 3 hours. The precipitated product was filtered and washed with ethylacetate and dried under vacuum 40-45° C. to get 3.1 gm of title product. XRD: 4.81, 7.13, 9.67, 14.56 and 17.45±0.2 degrees 2 theta, Purity by HPLC: 97.98%, Melting Range: 141-149° C.

Example 11

Crystalline Ivacaftor.n-Butanol Solvate

The crystalline ivacaftor n-butanol solvate of example 2 was subjected to drying under vacuum for a period of about 60 hours. Butanol content: 111475 ppm

XRD

| Pos. [°2Th.] | d-spacing [Å] | Rel. Int. [%] |
|---|---|---|
| 3.4 | 26.4 | 9.67 |
| 5.8 | 15.2 | 100 |
| 6.6 | 13.2 | 46.16 |
| 6.8 | 12.8 | 51.57 |
| 9.9 | 8.9 | 2.13 |
| 10.3 | 8.5 | 1.74 |
| 11.6 | 7.6 | 6.73 |
| 12.6 | 6.9 | 2.52 |
| 12.9 | 6.8 | 2.33 |
| 13.7 | 6.4 | 6.11 |
| 14.1 | 6.2 | 9.33 |
| 14.2 | 6.2 | 6.71 |
| 16.3 | 5.4 | 0.31 |
| 17.4 | 5 | 0.77 |
| 19 | 4.6 | 2.7 |
| 19.3 | 4.5 | 2.28 |
| 20 | 4.4 | 5.86 |
| 21.3 | 4.1 | 5.17 |
| 21.9 | 4 | 7 |
| 23.3 | 3.8 | 23.92 |
| 25.3 | 3.5 | 0.67 |
| 26.9 | 3.3 | 2.05 |
| 28.1 | 3.1 | 4.11 |
| 29.3 | 3 | 1.19 |
| 30.4 | 2.9 | 2.47 |
| 36.3 | 2.4 | 1.91 |
| 38.2 | 2.3 | 0.76 |

Example 12

Process for Preparation of Amorphous Ivacaftor

In a clean flask, 35.0 g ivacaftor methanol solvate and 350 ml of n-Butanol were charged. Reaction mass was heated to 80-85° C. to obtain clear solution. The reaction mass was stirred at 80-85° C. for 30 min and then gradually cooled to 25 to about 30° C. The reaction mass was stirred at 25 to about 30° C. for 60 to 120 min. The solid obtained was filtered and washed with n-Butanol. The ivacaftor.n-butanol solvate was dried for 60 hours to get semidried butanol solvate 27.5 gm. Chromatographic purity by HPLC—99.97, Butanol content: 95,340 ppm GC.

The semidried butanol solvate was dissolved in 308 ml methyl ethyl ketone and 18.48 ml of water and spray dried using following condition to obtain amorphous Ivacaftor Inlet temp: 85-95° C., Outlet temp: 65-75° C., Feed rate 30.0 ml/Min Ivacaftor.n-butanol solvate was dried in tray drier at 70-75° C. for 20-24 hours to get ivacaftor as an amorphous form. Yield 18.2 gms. Chromatographic purity by HPLC 99.98%

Example-13

Preparation of Ivacaftor Form D

In a clean round bottom flask 4-oxo-1,4-dihydroquinoline-3-carboxylic acid (5.0 gm), O-(7-azabenzotriazol-1-yl)-N,N,N',N'-tetramethyluronium hexafluorophosphate (HATU) (10.0 gm), di-isopropyl ethyl amine (10.0 ml) and dimethyl formamide (DMF) (25.0 ml) were charged. The reaction mass was stirred for about 30 minutes and 5-amino-2-4-di-tert-butyl-phenol (6.25 gm) was added to the reaction mass and stirred for a period of about 15.0 hr. Water was added to the reaction mass and the product was extracted with ethyl acetate. The ethyl acetate layer was concentrated under vacuum till one volume of ethyl acetate was left. To the above mixture a mixture of acetonitrile and water (50.0 ml; 9:1) was charged and the reaction mass was heated to about 60-65° C. The solution was stirred for about 30 minutes and cooled to a temperature of about 20-30° C. The precipitated product was filtered and dried to at 40-45° C. obtain 5.5 gm of ivacaftor Form D. HPLC purity 99.69%.

XRD Table of Ivacaftor Form D

| Pos [°2θ] | d-spacing [Å] | Rel Int [%] |
|---|---|---|
| 4.18 | 21.09 | 100 |
| 4.55 | 19.41 | 40.31 |
| 6.89 | 12.82 | 5.54 |
| 7.57 | 11.67 | 2.71 |
| 8.38 | 10.54 | 4.31 |
| 9.22 | 9.59 | 18.29 |
| 10.39 | 8.51 | 2.05 |
| 11.75 | 7.52 | 23.75 |
| 12.54 | 7.05 | 15.68 |
| 13.32 | 6.64 | 6 |
| 14.34 | 6.17 | 3.69 |
| 15.26 | 5.8 | 1.22 |
| 16.73 | 5.29 | 5.15 |
| 17.24 | 5.14 | 7.68 |
| 17.82 | 4.97 | 9.53 |
| 18.45 | 4.8 | 11.75 |
| 19.59 | 4.53 | 9.18 |
| 20.28 | 4.37 | 9.19 |
| 21.05 | 4.21 | 5.49 |
| 23.62 | 3.76 | 4.84 |
| 25.09 | 3.54 | 2.98 |
| 26.45 | 3.36 | 3.05 |
| 27.06 | 3.29 | 3.41 |
| 30.3 | 2.94 | 1.18 |
| 38.42 | 2.34 | 0.54 |

Example-14

Preparation of Ivacaftor Form E 4-oxo-1,4-dihydroquinoline-3-carboxylic acid (5.0 gm), O-(7-azabenzotriazol-1-yl)-N,N,N',N'-tetramethyluronium hexafluorophosphate (HATU) (12.0 gm), Di-isopropyl ethyl amine (12.5 ml) and DMF (25.0 ml) were charged to a reactor & stirred for 30 minutes. 5-amino-2-4-di-tert-butyl-phenol (6.25 gm) was added to the reaction mass and stirred for a period of about 15.0 hr to complete the reaction. Water was added to the reaction mass & product was extracted with ethyl acetate. The ethyl acetate layer was washed with brine solution & concentrated to remove it completely to get a semisolid. To the obtained semisolid, a mixture of acetonitrile and water (50.0 ml; 9:1) was charged and the reaction mass was heated to about 70-75° C. The solution was stirred for about 30 minutes and cooled to a temperature of about 20-30° C. The precipitated product was filtered and air oven dried at 25-30° C. to obtain 5.0 gm of ivacaftor polymorph E. HPLC purity 99.61%.

XRD Table of Ivacaftor Form E

| Pos [°2θ] | d spacing [Å] | Rel. Int % |
|---|---|---|
| 4.26 | 20.71 | 49.22 |
| 4.6 | 19.19 | 100 |
| 6.96 | 12.69 | 15.54 |
| 7.59 | 11.63 | 11.02 |
| 9.05 | 9.76 | 36.79 |
| 10.53 | 8.39 | 3.39 |
| 11.43 | 7.73 | 25.51 |
| 11.92 | 7.42 | 51.59 |
| 12.47 | 7.09 | 29.39 |
| 13 | 6.8 | 27.08 |
| 13.78 | 6.42 | 17.66 |
| 14.41 | 6.14 | 12.73 |
| 15.21 | 5.82 | 3.89 |
| 16.83 | 5.26 | 10.69 |
| 17.89 | 4.95 | 16.22 |
| 18.49 | 4.79 | 19.67 |
| 19.07 | 4.65 | 19.31 |
| 19.68 | 4.5 | 21.05 |
| 20.38 | 4.35 | 29.53 |
| 21.28 | 4.17 | 13.53 |
| 22.41 | 3.96 | 11.32 |
| 25.09 | 3.55 | 7.53 |
| 25.91 | 3.43 | 3.98 |
| 27.34 | 3.26 | 8.75 |
| 28.92 | 3.08 | 6.51 |
| 30.72 | 2.9 | 2.43 |
| 32.85 | 2.72 | 2.56 |
| 38.66 | 2.32 | 1.49 |

Example 15

Preparation of Ivacaftor Form E1

Ivacaftor Form E obtained in example 2 was further dried at 40-45° C. for 12 hours to get ivacaftor Form E1.

XRD Table of Ivacaftor Form E1

| Pos [°2θ] | d spacing [Å] | Rel. Int % |
|---|---|---|
| 4.48 | 19.72 | 100 |
| 6.82 | 12.94 | 11.58 |
| 7.45 | 11.85 | 6.87 |
| 8.86 | 9.97 | 16.83 |
| 9.28 | 9.52 | 10.67 |
| 9.66 | 9.15 | 4.94 |
| 10.3 | 8.58 | 1.93 |
| 11.28 | 7.84 | 13.23 |
| 11.73 | 7.54 | 28.95 |
| 12.39 | 7.14 | 12.82 |
| 12.81 | 6.90 | 14.24 |
| 13.68 | 6.47 | 10.59 |
| 14.19 | 6.23 | 7.8 |
| 15.09 | 5.87 | 2.82 |
| 16.76 | 5.28 | 5.59 |
| 17.68 | 5.01 | 6.76 |
| 18.87 | 4.7 | 8.87 |
| 19.53 | 4.54 | 9.73 |
| 20.22 | 4.39 | 15.94 |
| 21.14 | 4.2 | 7.62 |
| 22.37 | 3.97 | 8.53 |
| 24.91 | 3.57 | 3.9 |
| 25.61 | 3.47 | 2.92 |
| 27.14 | 3.28 | 4.61 |
| 28.59 | 3.12 | 4.39 |
| 29.56 | 3.02 | 2.48 |
| 32.7 | 2.73 | 2.02 |
| 36.3 | 2.47 | 0.54 |
| 38.32 | 2.34 | 0.87 |
| 40.87 | 2.2 | 0.73 |
| 43.13 | 2.09 | 0.83 |

Example 16

Preparation of 2,4-Di-Tert-Butyl-5-Nitrophenyl Methyl Carbonate

In a clean round bottom flask charge, 4-di-tert-butylphenol (10 gm.), triethyl amine (9.8 gm) and 4-dimethyl amino pyridine (0.3 gm) in 50.0 ml of dichloromethane. To this add methyl chloro format (6.40 gm) in reaction mass at 0-5 C. The reaction mass was maintained for 2.0 hr. The reaction mass was washed with water and dil hydrochloric acid solution followed by drying the organic layer with sodium sulphate. To organic layer sulphuric acid (20.80 gm) was charged and nitric acid (8.0 gm.) in at 0-5 C. The reaction mass was maintained for 90. Min and quenched in water. The organic layer was washed with 10% sodium chloride solution and concentrated to obtain residue. This was crystallized with 60.0 ml methanol and to get 4.0 gm, of title product. Chromatographic purity by HPLC 97.41%

Example 17

Preparation of 5-amino-2-4-di-tert-butyl-phenol

In a clean round bottom flask charge, 2,4-di-tert-butyl-5-nitrophenyl methyl carbonate (10.0 gm) and potassium hydroxide (2.71 gm) in 60.0 ml of methanol. The reaction mass was stirred for 2-3 hr and concentrated. To the residue water and ethyl acetate was added and pH was adjusted to 1.0 to 3.0 by con HCl. The organic layer was washed with 10% sodium chloride solution and then concentrated ethyl acetate toe get solid. The solid was dissolved in 50.0 ml of methanol and charge 10% palladium carbon (0.37 gm) in hydrogenater. To this a 5.0 to 6.0 kg Hydrogen pressure was applied and maintained for 2.0 hr at 25-30. The reaction mass was filtered and 50.0 ml water was added and maintained for 2.0 hr at 25-30 C. The reaction mass was filtered and purified with 40.0 ml of n-hexane to get 6.0 gm of title product. Chromatographic purity by HPLC 99.98%

Example 18

Preparation of Diethyl (Anilinomethylene) Malonate

In a clean round bottom flask charge aniline (10 gm), and di-ethyl (ethoxymethylene) malonate (2.40 gm). The reaction mass was heated to 50 55 C for 3.0 hr and cooled to 25-30 C. To this 80.0 ml of water was added. Again cool to 15-20 C and stir for 2.0 hr. Filter the product and wash with water to 25.0 gm title compound. Purity by HPLC—98.78%.

Example 19

Preparation of Ethyl 4-oxo-1,4-dihydroquinoline-3-carboxylate

In a clean round bottom flask, charge Diethyl (anilinomethylene) malonate (10.0 gm) and eaton's reagent (40.0 ml). The reaction mass was heated to 80-85 C for 10.0 hr and cooled to 25-30 C. To the reaction mass sodium carbonate solution was added at 25-30° C. and the product was filtered and washed with water and filtered. The wet cake was dissolved in acetone (80.0 ml) and water by heating to 45-50 C (10.0 ml) to obtain suspension. The solution was maintained for 1.0 hr, cooled to 25-30° C. and filtered. The product was dried at 50–55° C. for 24.0 hr to get 5.0 gm title compound. Purity by HPLC—99.32%

Example 20

Preparation of 4-oxo-1,4-dihydroquinoline-3-carboxylic acid

In a clean round bottom flask, ethyl 4-oxo-1,4-dihydroquinoline-3-carboxylate (10.0 gm) was charged to a solution of sodium hydroxide (17 gm) in 13.0 ml water. The reaction mass was heated for 3.0 hr at 80-85 C and then cooled to 25-30. To this was added 0.10 gm of activated charcoal and filtered. The pH was adjusted using con HCL and the product was filtered and washed with water. The wet cake slurried in methanol at 25-30 C and filtered. The product was dried under vacuum at 50.0 C to get 7.50 gm of title product Purity by HPLC—99.75%.

The invention claimed is:

1. A solvate of N-(2,4-di-tert-butyl-5-hydroxyphenyl-1,4-dihydro-4-oxoquiniline-3-carboxamide, a compound of formula I,

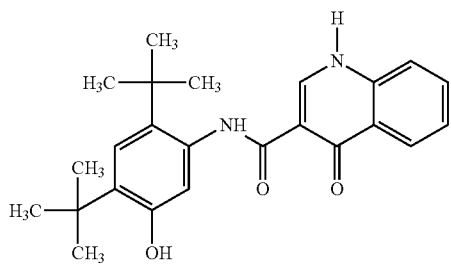

I

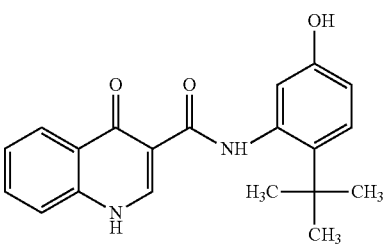

XII wherein the solvate is selected from a crystalline N-(2,4-di-tert-butyl-5-hydroxyphenyl)-1, 4-dihydro-4-oxoquiniline-3-carboxamide.n-butanol solvate characterized by X-ray Diffraction (XRD) spectrum having peak reflections at about 3.4 and 14.2±0.2 degrees 2 theta or a crystalline N-(2,4-di-tert-butyl-5-hydroxyphenyl)-1, 4-dihydro-4-oxoquiniline-3-carboxamide.methanol solvate characterized by X-ray Diffraction (XRD) spectrum having peak reflections at about 7.28, 13.84, 14.03, 19.78, 20.27 and 20.92±0.2 degrees 2 theta.

2. A process for the preparation of N-(2,4-di-tert-butyl-5-hydroxyphenyl)-1, 4-dihydro-4-oxoquiniline-3-carboxamide, a compound of formula I,

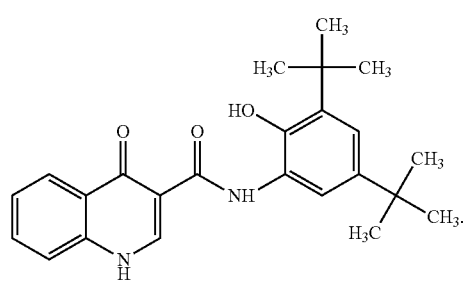

XIII

6. The process of claim 2, wherein N-(2,4-di-tert-butyl-5-hydroxyphenyl)-1, 4-dihydro-4-oxoquiniline-3-carboxamide in amorphous form is free from the listed genotoxic impurities, compounds of formula XI, II, VIII, XIV, VII, XV and XVI

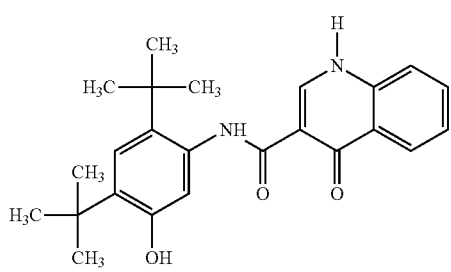

I

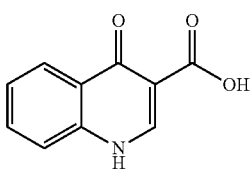

XI in amorphous form, the process comprising:
(a) dissolving the crystalline N-(2,4-di-tert-butyl-5-hydroxyphenyl)-1, 4-dihydro-4-oxoquiniline-3-carboxamide.n-butanol solvate or the crystalline N-(2,4-di-tert-butyl-5-hydroxyphenyl)-1, 4-dihydro-4-oxoquiniline-3-carboxamide.methanol solvate according to claim 1, in a solvent to form a solution; and
(b) removing the solvent from the solution obtained in (a).

3. The process of claim 2 wherein the solvent is selected from the group consisting of water, methyl ethyl ketone, n-butanol and mixtures thereof.

4. The process of claim 2, wherein in step (b) the solvent is removed by spray drying, fluid bed drying, lyophilization, flash drying, spin flash drying, or thin-film drying.

5. The process of claim 2, wherein a compound of formula XII or XIII is less than 0.1% w/w of amorphous N-(2,4-di-tert-butyl-5-hydroxyphenyl)-1, 4-dihydro-4-oxoquiniline-3-carboxamide as measured by high performance liquid chromatography.

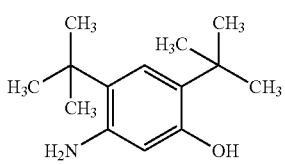

II

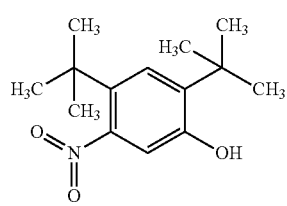

VIII

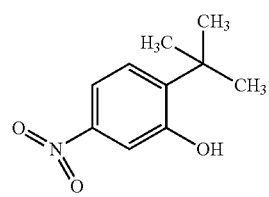

XIV

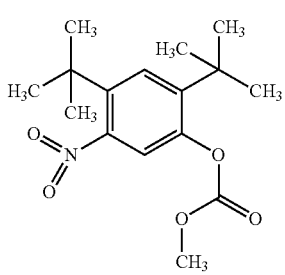

VII

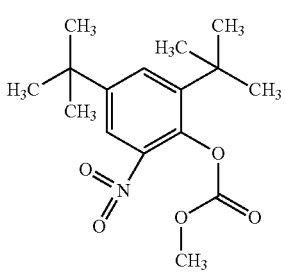

XV

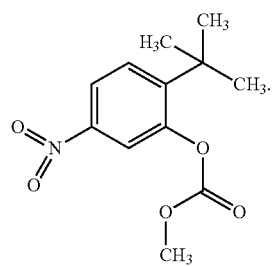

XVI

7. The process of claim 2 wherein the crystalline N-(2,4-di-tert-butyl-5-hydroxyphenyl)-1, 4-dihydro-4-oxoquiniline-3-carboxamide.n-butanol solvate is prepared by a process comprising:
   a) converting N-(2,4-di-tert-butyl-5-hydroxyphenyl)-1, 4-dihydro-4-oxoquiniline-3-carboxamide to the crystalline N-(2,4-di-tert-butyl-5-hydroxyphenyl)-1, 4-dihydro-4-oxoquiniline-3-carboxamide.methanol solvate; and
   b) converting the crystalline N-(2,4-di-tert-butyl-5-hydroxyphenyl)-1, 4-dihydro-4-oxoquiniline-3-carboxamide.methanol solvate to the crystalline N-(2,4-di-tert-butyl-5-hydroxyphenyl)-1, 4-dihydro-4-oxoquiniline-3-carboxamide.n-butanol solvate.

8. The process of claim 7, wherein N-(2,4-di-tert-butyl-5-hydroxyphenyl-1, 4-dihydro-4-oxoquiniline-3-carboxamide is prepared by a process comprising:
   a) converting a compound of formula IX to a compound of formula X

IX

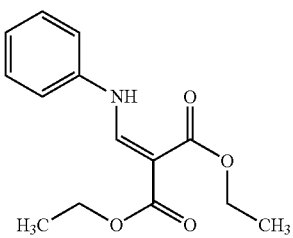

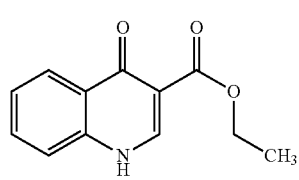

X in the presence of Eaton's reagent;
   b) hydrolysing the compound of formula X to obtain the compound of formula XI; and

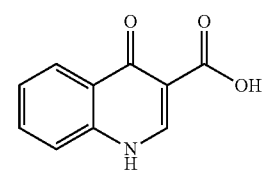

XI c) reacting the compound of formula XI with a compound of formula II to obtain N-(2,4-di-tert-butyl-5-hydroxyphenyl)-1, 4-dihydro-4-oxoquiniline-3-carboxamide.

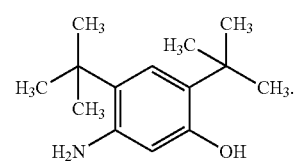

II

9. The process of claim 2 wherein the crystalline N-(2,4-di-tert-butyl-5-hydroxyphenyl)-1, 4-dihydro-4-oxoquiniline-3-carboxamide.n-butanol solvate is prepared by a process comprising:
   a) treating N-(2,4-di-tert-butyl-5-hydroxyphenyl)-1, 4-dihydro-4-oxoquiniline-3-carboxamide or a solvate thereof with a n-butanol;
   b) optionally, heating the above mixture of step (a);
   c) cooling the above mixture of step (b); and
   d) isolating the crystalline N-(2,4-di-tert-butyl-5-hydroxyphenyl)-1, 4-dihydro-4-oxoquiniline-3-carboxamide.n-butanol solvate.

10. The process of claim 2 wherein the crystalline N-(2,4-di-tert-butyl-5-hydroxyphenyl)-1, 4-dihydro-4-oxoquiniline-3-carboxamide methanol solvate is prepared by a process comprising:
   a) treating N-(2,4-di-tert-butyl-5-hydroxyphenyl)-1, 4-dihydro-4-oxoquiniline-3-carboxamide with methanol to obtain a mixture;
   b) optionally, heating the above mixture of step (a);
   c) cooling the above mixture of step (b); and
   d) isolating crystalline N-(2,4-di-tert-butyl-5-hydroxyphenyl)-1, 4-dihydro-4-oxoquiniline-3-carboxamide.methanol solvate.

11. The process of claim 2, comprising:
   a) dissolving crystalline N-(2,4-di-tert-butyl-5-hydroxyphenyl)-1, 4-dihydro-4-oxoquiniline-3-carboxamide.methanol solvate in n-butanol to form a solution; and
   b) removing the solvent from the solution by a process comprising:

i) filtering the solvent to obtain N-(2,4-di-tert-butyl-5-hydroxyphenyl-1, 4-dihydro-4-oxoquiniline-3-carboxamide.n-butanol solvate; and ii) drying the N-(2,4-di-tert-butyl-5-hydroxyphenyl)-1, 4-dihydro-4-oxoquiniline-3-carboxamide.n-butanol solvate to obtain amorphous N-(2,4-di-tert-butyl-5-hydroxyphenyl)-1, 4-dihydro-4-oxoquiniline-3-carboxamide.

12. The process of claim 11, wherein in step (b) (ii) drying is carried out at a temperature of 70 to 75° C. for a time period of 20 to 24 hours.

* * * * *